US012594268B2

(12) United States Patent
Benjamin

(10) Patent No.: US 12,594,268 B2
(45) Date of Patent: Apr. 7, 2026

(54) METHODS OF TREATING FABRY DISEASE IN PATIENTS HAVING A MUTATION IN THE GLA GENE

(71) Applicant: Amicus Therapeutics, Inc., Philadelphia, PA (US)

(72) Inventor: Elfrida Benjamin, Millstone Township, NJ (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 858 days.

(21) Appl. No.: 17/269,890

(22) PCT Filed: Jan. 16, 2019

(86) PCT No.: PCT/US2019/013761

§ 371 (c)(1),
(2) Date: Feb. 19, 2021

(87) PCT Pub. No.: WO2020/040806

PCT Pub. Date: Feb. 27, 2020

(65) Prior Publication Data

US 2021/0315875 A1 Oct. 14, 2021

Related U.S. Application Data

(60) Provisional application No. 62/719,962, filed on Aug. 20, 2018.

(51) Int. Cl.
*A61K 31/445* (2006.01)
*A61P 3/00* (2006.01)

(52) U.S. Cl.
CPC .............. *A61K 31/445* (2013.01); *A61P 3/00* (2018.01)

(58) Field of Classification Search
CPC ................................ A61K 31/445; A61P 3/00
See application file for complete search history.

(56) References Cited

U.S. PATENT DOCUMENTS

| | | | |
|---|---|---|---|
| 7,851,143 | B2 | 12/2010 | Kaneski et al. |
| 7,973,157 | B2 | 7/2011 | Major et al. |
| 8,321,148 | B2 | 11/2012 | Lockhart et al. |
| 8,592,362 | B2 | 11/2013 | Benjamin et al. |
| 9,000,011 | B2 | 4/2015 | Lockhart et al. |
| 9,056,101 | B2 | 6/2015 | Lockhart |
| 9,066,939 | B2 | 6/2015 | Schiffmann et al. |
| 9,095,584 | B2 | 8/2015 | Benjamin et al. |
| 9,206,457 | B2 | 12/2015 | Do |
| 9,480,682 | B2 | 11/2016 | Lockhart et al. |
| 9,545,397 | B2 | 1/2017 | Benjamin et al. |
| 9,694,056 | B2 | 7/2017 | Khanna et al. |
| 9,750,732 | B2 | 9/2017 | Schiffmann et al. |
| 9,987,263 | B2 | 6/2018 | Lockhart et al. |
| 9,999,618 | B2 | 6/2018 | Castelli et al. |
| 10,076,514 | B2 | 9/2018 | Benjamin |
| 10,155,027 | B2 | 12/2018 | Khanna et al. |
| 10,251,873 | B2 * | 4/2019 | Castelli ................ A61K 31/445 |
| 10,357,548 | B2 | 7/2019 | Khanna |
| 10,383,864 | B2 | 8/2019 | Lockhart et al. |
| 10,406,143 | B2 | 9/2019 | Lockhart et al. |
| 10,471,053 | B2 | 11/2019 | Castelli et al. |
| 10,525,045 | B2 | 1/2020 | Castelli et al. |
| 10,537,564 | B2 | 1/2020 | Benjamin |
| 10,792,278 | B2 * | 10/2020 | Castelli ................... A61P 13/12 |
| 10,792,279 | B2 * | 10/2020 | Castelli ................... A61P 13/12 |
| 10,799,491 | B2 * | 10/2020 | Castelli ................ A61K 31/445 |
| 10,806,727 | B2 | 10/2020 | Castelli et al. |
| 10,813,921 | B2 | 10/2020 | Benjamin et al. |
| 10,849,889 | B2 * | 12/2020 | Castelli ................... A61P 13/12 |
| 10,849,890 | B2 * | 12/2020 | Castelli ................ A61K 31/445 |
| 10,857,141 | B2 * | 12/2020 | Castelli ................ A61K 31/445 |
| 10,857,142 | B2 * | 12/2020 | Castelli ................ A61K 31/445 |
| 10,874,655 | B2 * | 12/2020 | Castelli ................... A61P 13/12 |
| 10,874,656 | B2 * | 12/2020 | Castelli ................ A61K 31/445 |
| 10,874,657 | B2 * | 12/2020 | Castelli ................ A61K 31/445 |
| 10,925,866 | B2 | 2/2021 | Castelli et al. |
| RE48,608 | E | 6/2021 | Benjamin et al. |
| 11,234,972 | B2 | 2/2022 | Benjamin |

(Continued)

FOREIGN PATENT DOCUMENTS

| | | | |
|---|---|---|---|
| WO | 2007137072 | A2 | 11/2007 |
| WO | 2008045015 | A1 | 4/2008 |

(Continued)

OTHER PUBLICATIONS

GALAFOLD, "Prescribing Information GALAFOLD", 2018, FDA.gov, pp. 1-29 (Year: 2018).*

GALAFOLD, Summary of Product Characteristics, Aug. 18, 2018 (Year: 2018).*

Elfrida, Benjamin R., et al., "The validation of pharmacogenetics for the identification of Fabry patients to be treated with migalastat", Genetics in Medicine, vol. 19, No. 4, Sep. 22, 2016 (Sep. 22, 2016), pp. 430-438, XP055582063, US ISSN: 1098-3600, D0I: 10. 1038/gim.2016. 122 table 11SA.

Sang, Shin H., "Prediction of Response of Mutated a-GALACTOSIDASE A to a Pharmacological Chaperone", Pharmacogenetics and Genomics, Lippincott Williams & Wilkins, Philadelphia, PA, US, vol. 18, No. 9, Sep. 1, 2008, pp. 773-780.

(Continued)

*Primary Examiner* — Brenda L Coleman
*Assistant Examiner* — Madeline E Braun
(74) *Attorney, Agent, or Firm* — SERVILLA WHITNEY LLC

(57) ABSTRACT

Provided are methods of treating a patient diagnosed with Fabry disease and methods of enhancing α-galactosidase A in a patient diagnosed with or suspected of having Fabry disease. Certain methods comprise administering to a patient a therapeutically effective dose of a pharmacological chaperone for α-galactosidase A, wherein the patient has a mutation in the nucleic acid sequence encoding α-galactosidase A. Also described are uses of pharmacological chaperones for the treatment of Fabry disease and compositions for use in the treatment of Fabry disease.

9 Claims, 6 Drawing Sheets

Specification includes a Sequence Listing.

(56) References Cited

U.S. PATENT DOCUMENTS

| | | | | |
|---|---|---|---|---|
| 11,241,422 | B2 | 2/2022 | Lockhart et al. | |
| 11,278,536 | B2 * | 3/2022 | Castelli | A61P 13/12 |
| 11,278,537 | B2 * | 3/2022 | Castelli | A61P 13/12 |
| 11,278,538 | B2 * | 3/2022 | Castelli | A61K 31/445 |
| 11,278,539 | B2 * | 3/2022 | Castelli | A61K 31/445 |
| 11,278,540 | B2 * | 3/2022 | Castelli | A61P 13/12 |
| 11,304,940 | B2 | 4/2022 | Castelli et al. | |
| 11,357,761 | B2 * | 6/2022 | Castelli | A61P 13/12 |
| 11,357,762 | B2 * | 6/2022 | Castelli | A61P 13/12 |
| 11,357,763 | B2 * | 6/2022 | Castelli | A61P 13/12 |
| 11,357,764 | B1 | 6/2022 | Castelli et al. | |
| 11,357,765 | B1 | 6/2022 | Castelli et al. | |
| 11,357,784 | B2 | 6/2022 | Barth | |
| 11,376,244 | B2 | 7/2022 | Castelli et al. | |
| 11,389,436 | B2 | 7/2022 | Castelli et al. | |
| 11,389,437 | B2 * | 7/2022 | Castelli | A61P 13/12 |
| 11,426,396 | B2 | 8/2022 | Castelli et al. | |
| 11,458,128 | B2 | 10/2022 | Castelli et al. | |
| 11,612,593 | B2 | 3/2023 | Castelli et al. | |
| 11,612,594 | B2 | 3/2023 | Castelli et al. | |
| 11,622,962 | B2 | 4/2023 | Castelli et al. | |
| 11,633,387 | B2 | 4/2023 | Castelli et al. | |
| 11,633,388 | B2 * | 4/2023 | Castelli | A61P 13/12 514/315 |
| 11,642,334 | B2 * | 5/2023 | Castelli | A61P 13/12 514/315 |
| 11,666,564 | B2 * | 6/2023 | Castelli | A61K 31/445 514/315 |
| 11,786,516 | B2 | 10/2023 | Castelli et al. | |
| 11,813,255 | B2 | 11/2023 | Castelli et al. | |
| 11,826,360 | B2 | 11/2023 | Castelli et al. | |
| 11,833,164 | B2 | 12/2023 | Benjamin et al. | |
| 2011/0152319 | A1 | 6/2011 | Banjamin et al. | |
| 2014/0219986 | A1 | 8/2014 | Greene et al. | |
| 2017/0051267 | A1 | 2/2017 | Calhoun | |
| 2018/0153999 | A1 | 6/2018 | Greene et al. | |
| 2018/0360812 | A1 | 12/2018 | Castelli et al. | |
| 2018/0360814 | A1 | 12/2018 | Castelli et al. | |
| 2019/0000818 | A1 | 1/2019 | Benjamin et al. | |
| 2019/0183869 | A1 | 6/2019 | Castelli | |
| 2019/0358302 | A1 | 11/2019 | Gotcschall | |
| 2019/0388409 | A1 | 12/2019 | Lockhart et al. | |
| 2020/0215043 | A1 | 7/2020 | Benjamin | |
| 2020/0222377 | A1 | 7/2020 | Castelli et al. | |
| 2020/0268890 | A1 | 8/2020 | Greene et al. | |
| 2021/0030730 | A1 | 2/2021 | Castelli et al. | |
| 2021/0038579 | A1 | 2/2021 | Barth et al. | |
| 2021/0038581 | A1 | 2/2021 | Castelli et al. | |
| 2021/0038582 | A1 | 2/2021 | Castelli et al. | |
| 2021/0038583 | A1 * | 2/2021 | Castelli | A61P 13/12 |
| 2021/0038624 | A1 | 2/2021 | Barth | |
| 2021/0038625 | A1 | 2/2021 | Benjamin et al. | |
| 2021/0069161 | A1 | 3/2021 | Castelli et al. | |
| 2021/0069162 | A1 | 3/2021 | Castelli | |
| 2021/0085660 | A1 | 3/2021 | Castelli et al. | |
| 2021/0085661 | A1 | 3/2021 | Castelli et al. | |
| 2021/0251971 | A1 | 8/2021 | Benjamin et al. | |
| 2021/0251972 | A1 * | 8/2021 | Skuban | A61P 9/10 |
| 2021/0315875 | A1 | 10/2021 | Benjamin | |
| 2022/0087993 | A1 * | 3/2022 | Skuban | A61P 9/10 |
| 2023/0136297 | A1 * | 5/2023 | Benjamin | A61P 3/00 514/315 |
| 2023/0218599 | A1 * | 7/2023 | Castelli | A61P 13/12 514/315 |

FOREIGN PATENT DOCUMENTS

| | | | |
|---|---|---|---|
| WO | 2008134628 | A3 | 11/2008 |
| WO | 2009102895 | A3 | 8/2009 |
| WO | 2010048532 | A1 | 4/2010 |
| WO | 2010138608 | A1 | 12/2010 |
| WO | 2011063048 | A2 | 5/2011 |
| WO | 2012071451 | A2 | 5/2012 |
| WO | 2012125402 | A3 | 9/2012 |
| WO | 2012/154681 | A1 | 11/2012 |
| WO | 2013/091897 | A1 | 6/2013 |
| WO | 2014014938 | A1 | 1/2014 |
| WO | 2017165164 | A1 | 9/2017 |
| WO | 2018017721 | A1 | 1/2018 |
| WO | 2018132471 | A1 | 7/2018 |
| WO | 2018222655 | A1 | 12/2018 |
| WO | 2019017938 | A1 | 1/2019 |
| WO | 2019046244 | A1 | 3/2019 |
| WO | 2019157047 | A1 | 8/2019 |
| WO | 2019157056 | A1 | 8/2019 |
| WO | 2020040806 | A1 | 2/2020 |
| WO | 2020252129 | A1 | 12/2020 |

OTHER PUBLICATIONS

Lukas, Jan , et al., “Functional and Clinical Consequences of Novel α-Galactosidase A Mutations in Fabry Disease”, Human Mutation, vol. 37, No. 1, 43-51, 2016.

Benjamin , et al., “The Validation of Pharmacogenetics for the Identification of Fabry Patients for Treatment with Migalastat”, Supplementary Information (2017).

Benjamin, Elfrida R., et al., “The validation of pharmacogenetics for the identification of Fabry patients to be treated with migalastat”, Genetics in Medicine, vol. 19, No. 4, Sep. 22, 2016 (Sep. 22, 2016), pp. 430-438, XP055582063, US ISSN: 1098-3600, D0I: 10. 1038/gim.2016. 122 table 11SA.

Bichet, D. G., et al., “Persistence of Positive Renal and Cardiac Effects of Migalastat in Fabry Patients with Amenable Mutations Following 30 Months of Treatment in the ATTRACT Study”, Posters at WORLDSymposium™ 2016, Mar. 1, 2016.

Brennan, Paul , et al., “Case-finding in Fabry disease: experience from the North of England”, J Inherit Metab Dis (2014) 37:103-107 DOI 10.1007/s10545-013-9629-8.

Brennan, P. , et al., “Case-finding in Fabry disease: experience from the North of England”, Supplementary Online Material (2014).

Citro, Valentina , et al., “The Large Phenotypic Spectrum of Fabry Disease Requires Graduated Diagnosis and Personalized Therapy: A Meta-Analysis Can Help to Differentiate Missense Mutations”, Int. J. Mol. Sci. 2016, 17, 2010.

Csányi, Beáta, et al., “Identification of a Novel GLA Gene Mutation, p.Ile239Met, in Fabry Disease With a Predominant Cardiac Phenotype”, Novel p.Ile239Met GLA Mutation in Fabry Disease, vol. 158, No. 3, May 2017.

Desnick , et al. , “Posters Metabolic Disorders”, The American Society of Human Genetics (2015).

Dobrovolny, Robert , et al., “Relationship between X-inactivation and clinical Involvement in Fabry heterozygotes, Eleven novel mutations in the a-galactosidase A gene in the Czech and Slovak population”, J Mol Med (2005) 83: 647-654 DOI 10. 1007/s00109-005-0656-2.

Doi, Kent , et al., “High-throughput screening identified disease-causing mutants and functional variants of a-galactosidase A gene in Japanese male hemodialysis patients”, Journal of Human Genetics (2012) 57, 575-579.

Ebrahim, Hatim Y., et al., “Functional analysis of variant lysosomal acid glycosidases of Anderson-Fabry and Pompe disease in a human embryonic kidney epithelial cell line (HEK 293 T)”, J Inherit Metab Dis (2012) 35:325-334.

Echevarria, L. , et al., “X-chromosome inactivation in female patients with Fabry disease”, Clinical Genetics 2016: 89: 44-54.

Fan, Jian-Qiang , et al., “Accelerated transport and maturation of lysosomal alpha-galactosidase A in Fabry lymphoblasts by an enzyme inhibitor”, Nat. Med. Vol. 5 No. 1, 1999, 112-115.

Favalli, Valentina , et al., “Genetic Screening of Anderson-Fabry Disease in Probands Referred From Multispecialty Clinics”, Journal of the American College of Cardiology, vol. 68, No. 10, 2016.

Feldt-Rasmussen, U. , et al., “Response of Patients With Fabry Disease With the Amenable GLA Mutation p.N215S to Treatment With Migalastat”, Presented at the 13th International Congress of Inborn Errors of Metabolism; Sep. 5-8, 2017; Rio de Janeiro, Brazil.

Froissart, Roseline , et al., “Fabry disease: D313Y is an a-galactosidase A sequence variant that causes pseudodeficient activity in plasma”, Molecular Genetics and Metabolism 80 (2003) 307-314.

(56) References Cited

OTHER PUBLICATIONS

Fukutomi, Motoki , et al., "Japanese patients with Fabry disease predominantly showing cardiac and neurological manifestation with novel missense mutation: R220P", Journal of Cardiology 62 (2013) 63-69.
Galafold , "Prescribing Information Galafold", Retrieved from the Internet: URL :https: //www.accessdata.fda.gov/drugsatfda_docs/ label/2018/2086231 bl.pdf [retrieved on Apr. 24, 2019] table 2, Aug. 1, 2018, pp. 1-29.
Garman, Scott C., et al., "Structural basis of Fabry disease", Molecular Genetics and Metabolism 77 (2002) 3-11.
Garman, Scott C., et al., "The Molecular Defect Leading to Fabry Disease: Structure of Human a-Galactosidase", J. Mol. Biol. (2004) 337, 319-335.
Gere, Sunder-Plassmann , et al., "Migalastat for the treatment of Fabry disease", Expert Opinion on Orphan Drugs, vol. 6, No. 5, May 4, 2018 (may 4, 2018), pp. 301-309, XP055527565, D0I:10. 1080/21678707.2018.1469978 Section 9. Regulatory affairs.
Germain, Dominique P., et al., "Efficacy of the pharmacologic chaperone migalastat in a subset of male patients with the classic phenotype of Fabry disease and migalastat-amenable variants: data from the phase 3 randomized, multicenter, double-blind clinical trial and extension study", Genetics in Medicine, vol. 21, No. 9, Feb. 6, 2019, 1987-1997.
Germain, Dominique P., et al., "Safety and pharmacodynamic effects of a pharmacological chaperone on !-galactosidase A activity and globotriaosylceramide clearance in Fabry disease: report from two phase 2 clinical studies", Orphanet Journal of Rare Diseases 2012, 7:91, 1-11.
Germain, Dominique P., et al., "Safety and pharmacodynamic effects of a pharmacological chaperone on a-glactosidase A. activity and globotriaosylceramide clearance in Fabry disease: report from two phase 2 clinical studies", Orphanet Journal of Rare Diseases 7:91, 2012, 11 pgs.
Germain, D.P. , et al., "Treatment of Fabry's Disease with the Pharmacologic Chaperone Migalastat", The New England Journal of Medicine 375;6, Aug. 11, 2016, 545-555.
Giugliani, R. , et al., "A Phase 2 study of migalastat hydrochloride in females with Fabry disease: Selection of population, safety and pharmacodynamic effects", Molecular Genetics and Metabolism 109, 2013, 86-92.
Haninger-Vacariu, Natalja , et al., "Pregnancy Outcome After Exposure to Migalastat: A Case Study", Molecular Genetics and Metabolism, Academic Press, Amsterdam, NL, vol. 123, No. 2, Feb. 6, 2018.
Havndrup, Ole , et al., "Fabry disease mimicking hypertrophic cardiomyopathy: genetic screening needed for establishing the diagnosis in women", European Journal of Heart Failure (2010) 12, 535-540.
Hughes, Derralynn A., et al., "Oral pharmacological chaperone migalastat compared with enzyme replacement therapy in Fabry disease: 18-month results from the randomised phase III ATTRACT study", J Med Genet 2017; 54, Nov. 10, 2016, 288-296.
Hughes, D. , et al., "Phenotype of Fabry Disease in Patients with Mutations Amenable to Migalastat", Posters at WORLDSymposium™ 2016, Mar. 1, 2016.
Hughes, D. A., et al., "Response of Patients With Fabry Disease With the Amenable GLA Mutation p.N215S to Treatment With Migalastat (ATTRACT Study)", Presented at the 13th Annual WORLDSymposium, Feb. 13-17, 2017, San Diego, CA, 1 page.
Ichinose, Mayuri , et al., "Significance of screening for Fabry disease among male dialysis patients", Clin Exp Nephrol (2005) 9:228-232.
Ishii, Satoshi , et al., "Role of Ser-65 in the activity of a-galactosidase A: characterization of a point mutation (S65T) detected in a patient with Fabry disease", Archives of biochemistry and biophysics, 377(2), May 15, 2000 (May 15, 2000), 228-233.
Iwafuchi, Yoichi , et al., "Enzyme replacement therapy in a patient of heterozygous Fabry disease: clinical and pathological evaluations by repeat kidney biopsy and a successful pregnancy", CEN Case Rep (2017) 6:210-214.
Johnson, Franklin K., et al., "An Open-Label Study to Determine the Pharmacokinetics and Safety of Migalastat HCl in Subjects with Impaired Renal Function and Healthy Subjects with Normal Renal Function", American College of Clinical Pharmacology, Clinical Pharmacology in Drug Development 2015, 4(4) 256-261.
Johnson, Britt , et al., "Analysis of Lyso-Globotriaosylsphingosine in Dried Blood Spots", Ann Lab Med 2013;33:274-278.
Johnson, F. K., et al., "Comparison of Integrated White Blood Cell Alpha-Galactosidase A Activity Exposure Between Every-Other-Day Orally Administered Migalastat and Biweekly Infusions of Agalsidase Beta or Agalsidase Alfa", Posters at WORLDSymposium™ 2016, Mar. 1, 2016.
Johnson, F. K., et al., "Pharmacokinetic Simulation of a 150-mg Every Other Day Dose Regimen for the Pharmacological Chaperone Migalastat HCl in Fabry Disease", Presented at the 2017 College of Clinical Pharmacology Annual Meeting, Sep. 17-19, 2017, San Diego, CA, 1 page.
Kawano, Makoto , et al., "Significance of Asymmetric Basal Posterior Wall Thinning in Patients With Cardiac Fabry's Disease", The American Journal of Cardiology (2007).
Khanna, Richie , et al., "Co-Administration of the Pharmacological Chaperone AT2221 with a Proprietary Recombinant Human Acid Alpha-Glucosidase Leads to Greater Plasma Exposure and Substrate Reduction Compared to Alglucosidase Alfa", Posters at WORLDSymposium™ 2016, Mar. 1, 2016.
Kobayashi, H. , et al., "A retrospective ESI-MS/MS analysis of newborn blood spots from 18 symptomatic patients with organic acid and fatty acid oxidation disorders diagnosed either in infancy or in childhood", J Inherit Metab Dis Short Report #065 (2007).
Koulousios, Konstantinos , et al., "Fabry disease due to D313Y and novel GLA mutations", BMJ Open 2017;7:e017098. doi:10.1136/ bmjopen-2017-017098.
Kroepfl, Th. , et al., "A novel 6 bp insertion in exon 7 associated with an unusual phenotype in a family with Fabry disease", J. Inherit. Metab. Dis. 25 (2002) 695-696.
Lee, Sheng-Hung , et al., "High-throughput detection of common sequence variations of Fabry disease in Taiwan using DNA mass spectrometry", Molecular Genetics and Metabolism 111 (2014) 507-512.
Liao, Hsuan-Chieh , et al., "Detecting multiple lysosomal storage diseases by tandem mass spectrometry—A national newborn screening program in Taiwan", Clinica Chimica Acta 431 (2014) 80-86.
Liao, Hsuan-Chieh , et al., "Functional and biological studies of α-galactosidase A variants with uncertain significance from newborn screening in Taiwan", Molecular Genetics and Metabolism 123 (2018) 140-147.
Lin, Hsiang-Yu , et al., "Clinical observations on enzyme replacement therapy in patients with Fabry disease and the switch from agalsidase beta to agalsidase alfa", Journal of the Chinese Medical Association xx (2013) 1-8.
Lin, Hsiang-Yu , et al., "High Incidence of the Cardiac Variant of Fabry Disease Revealed by Newborn Screening in the Taiwan Chinese Population", Circ Cardiovasc Genet, Oct. 2009, pages, pp. 450-456.
J Inherit Metab Dis (2007) 30 (Supple 1).
"A Phase 2, Open-Label, Multicenter, Ascending-Dose, 12-Week Study to Evaluate the Safety, Tolerability, Pharmacokinetics, and Pharmacodynamics of AT1001 in Patients with Fabry Disease", ClinicalTrials.gov Archive, Sep. 21, 2005.
"A Phase 2, Open-Label, Multiple Dose Level, 12-Week Study to Evaluate the Safety, Tolerability, and Pharmacodynamics of AT1001 in Female Patients With Fabry Disease", ClinicalTrials.gov Archive, Mar. 17, 2006.
"A Phase 2, Open-Label, Multiple Dose Level, 12-Week Study to Evaluate the Safety, Tolerability, and Pharmacodynamics of AT1001 in Female Patients with Fabry Disease", EU Clinical Trials Register, Feb. 13, 2013.

(56) References Cited

OTHER PUBLICATIONS

"A Phase 2, Open-Label, Single Dose Level, 12-Week Study to Evaluate the Safety, Tolerability, and Pharmacodynamics of AT1001 in Patients With Fabry Disease", ClinicalTrials.gov Archive, Jan. 30, 2006.
"A Phase 2, Open-Label, Single Dose Level, 24-Week Study to Evaluate the Safety, Tolerability, and Pharmacodynamics of AT1001 in Patients With Fabry Disease", ClinicalTrials.gov Archive, Jan. 30, 2006.
"A Phase 2, Open-Label, Single Dose Level, 24-Week Study to Evaluate the Safety, Tolerability, and Pharmacodynamics of AT1001 in Patients with Fabry Disease", EU Clinical Trials Register, Oct. 17, 2005.
"Amicus Therapeutics Announces Positive Phase 3 Data From Fabry Monotherapy Study 012", Amicus Therapeutics Press Release, Aug. 20, 2014.
"Amicus Therapeutics Announces Presentations and Posters at 12th Annual WORLDSymposium™ 2016", Amicus Therapeutics Press Release, Feb. 10, 2016.
Amicus Therapeutics, Current Report Pursuant to Section 13 or 15(d) of the Securities Exchange Act of 1934 (Form 8-K) (Mar. 3, 2016).
Galafold EP Label Summary of Product Characteristics, Feb. 2021, 59 pgs.
Galafold EP Label Summary of Product Characteristics, May 2022, 59 pages.
Galafold Product Information, Dec. 2021, 28 pages.
Galafold Product Information (original version), May 30, 2016, 45 pages.
Galafold Summary of Product Characteristics, Aug. 14, 2018, 49 pages.
Galafold Summary of Product Characteristics, Feb. 2021, 28 pages.
Galafold U.S. Label, Revised Aug. 10, 2018, 24 pages.
"Long-Term Migalastat Treatment Stabilizes Renal Function in Patients With Fabry Disease: Results From a Phase 3 Clinical Study (AT1001-041)", Presented at the 13th International Congress of Inborn Errors of Metabolism; Sep. 5-8, 2017; Rio de Janeiro, Brazil, 1 page.
Lukas 2013 Supplementary Table.
"MSDS—Deoxygalactonojirimycin (hydrochloride)", according to Regulation (EC) No. 1907/2006 as amended by (EC) No. 2015/830 and US OSHA HCS 2015, 1-5.
PCT Application No. PCT/US20/14531; Filed Jan. 22, 2020. "Methods of Reducing Cerebrovascular Events in Patients With Fabry Disease".
PCT International Search Report and Written Opinion in PCT/US2018/035032 dated Sep. 27, 2018, 18 pages.
PCT International Search Report and Written Opinion in PCT/US2019/013761 dated Jul. 3, 2019, 18 pages.
PCT International Search Report in PCT/US2019/016841 dated Apr. 30, 2019, 12 pages.
U.S. Appl. No. 17/148,817, filed Jan. 14, 2021, 170 pages.
U.S. Appl. No. 16/222,305, filed Dec. 17, 2018. "Method to Predict Response to Pharmacological Chaperone Treatment of Diseases".
U.S. Appl. No. 16/642,620, filed Feb. 27, 2020. "Methods of Enhancing and/or Stabilizing Cardiac Function in Patients With Fabry Disease".
U.S. Appl. No. 16/678,183, filed Nov. 8, 2019. "Methods of Treating Fabry Patients Having Renal Impairment".
U.S. Appl. No. 16/744,884, filed Jan. 16, 2020. "Methods of Treating Fabry Disease in Patients Having the G9331A Mutation in the GLA Gene".
U.S. Appl. No. 16/806,404, filed Mar. 2, 2020. "Dosing Regimens for the Treatment of Fabry Disease".
U.S. Appl. No. 16/817,877, filed Mar. 13, 2020. "Methods of Treating Fabry Patients Having Renal Impairment".
U.S. Appl. No. 16/817,881, filed Mar. 13, 2020. "Methods of Treating Fabry Patients Having Renal Impairment".
U.S. Appl. No. 16/817,888, filed Mar. 13, 2020. "Methods of Treating Fabry Patients Having Renal Impairment".
U.S. Appl. No. 16/817,895, filed Mar. 13, 2020. "Methods of Treating Fabry Patients Having Renal Impairment".
U.S. Appl. No. 16/817,900, filed Mar. 13, 2020. "Methods of Treating Fabry Patients Having Renal Impairment".
U.S. Appl. No. 16/817,908, filed Mar. 13, 2020. "Methods of Treating Fabry Patients Having Renal Impairment".
U.S. Appl. No. 16/817,911, filed Mar. 13, 2020. "Methods of Treating Fabry Patients Having Renal impairment".
U.S. Appl. No. 16/817,918, filed Mar. 13, 2020. "Methods of Treating Fabry Patients Having Renal Impairment".
U.S. Appl. No. 16/817,925, filed Mar. 13, 2020. "Methods of Treating Fabry Patients Having Renal Impairment".
U.S. Appl. No. 16/817,927, filed Mar. 13, 2020. "Methods of Treating Fabry Patients Having Renal Impairment".
U.S. Appl. No. 17/076,336, filed Oct. 21, 2020. "Methods of Treating Fabry Patients Having Renal Impairment".
U.S. Appl. No. 17/077,393, filed Oct. 22, 2020. "Methods of Treating Fabry Patients Having Renal Impairment".
Ashley, Grace Ann, "a-Galactosidase A: Mutation analysis in patients with Fabry disease and expression and regulation in transgenic mice", A dissertation submitted to the Graduate Faculty of the Mount Sinai Graduate School of Biological Sciences, Biomedical Sciences Doctoral Program (2001).
Ataides, Thiago Lacerda, et al., "Clinical Nephrology, Primary and Secondary Glomerulonephritis—1", Nephrology Dialysis Transplantation 30 (Supplement 3): iii104-iii124, 2015 doi:10.1093/ndt/gfv171.55.
Benjamin, E. R., et al., "The pharmacological ellaperone 1-deoxygalactonojirimycin Increases a-galactosidase A levels in Fabry patient cell lines", J Inherit Metab Dis (2009 ) 32:424-440 DOT I(U007/sl0545-009-1 077-0.
Lukas, Jan , et al., "Functional and Clinical Consequences of Novel Alpha-Galactosidase A Mutations in Fabry Disease", Human Mutation, vol. 0, No. 0, Sep. 29, 2015, 1-9.
Lukas, Jan , et al., "Functional Characterisation of Alpha-Galactosidase A Mutations as a Basis for a New Classification System in Fabry Disease", PLOS Genetics, vol. 9. Issue 8,(e1003632), Aug. 1, 2013, 1-10.
Malesci, Duccio , et al., "Malattia Di Fabry E Nuove Varianti Del Gene GLA: L'>Importanza Degli Studi Funzionali", Premio Simmesn 2015 per il Miglior Poster, 1 page.
Matsuda, Mitsuhiro , et al., "Novel G144D mutation of the GLA gene in a Chinese patient with Fabry disease", The Journal of Dermatology 2014.
Matsuzawa, Fumiko , et al., ""Fabry disease: correlation between structural changes in [alpha]-galactosidase, and clinical and biochemical phenotypes",", Human Genetics, Springer, Berlin, DE, vol. 117, No. 4, Aug. 1, 2005, 317-328.
Mehta, A , et al., "Enzyme replacement therapy with agalsidase alfa in patients with Fabry's disease: an analysis of registry data", Lavet 2009, vol. 374: 1986-96.
Mignani, Renzo , et al., "Agalsidase therapy in patients with Fabry disease on renal replacement therapy: a nationwide study in Italy", Nephrol Dial Transplant (2008) 23: 1628-1635, Dec. 5, 2007.
Mills, K. , et al., "Measurement of urinary CDH and CTH by tandem mass spectrometry in patients hemizygous and heterozygous for Fabry disease", J. Inherit. Metab.Dis. 28 (2005) 3548.
Najafian, B. , et al., "Six months of Migalastat Treatment Reduces Podocyte Globotriaosylceramide Content in Adult Male Patients with Fabry Disease", Posters at WORLDSymposium™ 2016, Mar. 1, 2016.
Nakagawa, Naoki , et al., "Clinical and Genetic Investigation of a Japanese Family With Cardiac Fabry Disease", Int Heart J, vol. 52, No. 5, Sep. 2011.
Namazova-Baranova, Leyla Seymurovna, et al., "Fabry disease in children: a federal screening programme in Russia", Eur J Pediatr (2017) 176:1385-1391.
Narita, Ichiei , et al., "Efficacy and safety of migalastat in a Japanese population: a subgroup analysis of the ATT RAC T study", Clinical and Experimental Nephrology (2020) 24, Dec. 30, 2019, 157-166.
Nicholls, K. , et al., "Renal Outcomes With Up to 9 Years of Migalastat in Patients With Fabry Disease: Results From an Open-

(56) References Cited

OTHER PUBLICATIONS label Extension Study", Presented at the 14th Annual WORLDSymposium, Feb. 5-9, 2018, San Diego, CA, 1 page.
Okumiya, Toshika , et al., "Galactose Stabilizes Various Missense Mutants of «-Galactosidase in Fabry Disease", Biochemical and Biophysical Research Communications, vol. 214, No. 3, Sep. 25, 1995, pp. 1219-1224.
Okur, Ilyas , et al., "Screening for Fabry disease in patients undergoing dialysis for chronic renal failure in Turkey: identification of new case with novel mutation", Gene 527(2013)42-47.
Pan, Xiaoxia , et al., "Genotype: A Crucial but Not Unique Factor Affecting the Clinical Phenotypes in Fabry Disease", PLoS ONE 11(8): e0161330.
Pereira, F.S. , et al., "Genomic analysis of Brazilian patients with Fabry disease", Brazilian Journal of Medical and Biological Research (2007) 40: ISSN 0100-879X.
Prabakaran, Thaneas , et al., "Long-term enzyme replacement therapy is associated with reduced proteinuria and preserved proximal tubular function in women with Fabry disease", Nephrol Dial Transplant (2014) 29: 619-625.
Ranieri, Michela , et al., "Fabry Disease: Recognition, Diagnosis, and Treatment of Neurological Features", Curr Treat Options Neurol (2016) IS: 33.
Saito, Seiji , et al., "Comparative Study of Structural Changes Caused by Different Substitutions at the Same Residue on a-Galactosidase A", PLoS ONE 8(12): e84267. doi:10.1371/journal.pone.0084267.
Sakac, Dejan , et al., "Fabry disease, do we think enough about this multisystemic disorder?—A presentation of three cases in a Serbial family", Vojnosanit Pregl 2012; 69(7): 620-622.
Savostyanov, K.V. , et al., "The New Genome Variants in Russian Children with Genetically Determined Cardiomyopathies Revealed with Massive Parallel Sequencing", Annals of the Russian Academy of Medical Sciences. 2017;72 (4):242-253.
Schiffmann, R , et al., "Cardiac Outcomes With Long-term Migalastat Treatment in Patients With Fabry Disease: Results From Phase 3 Trials", 2018.
Schiffmann, R. , et al., "Long-Term Migalastat Treatment Stabilizes Renal Function in Patients With Fabry Disease: Results from a Phase 3 Clinical Study (AT1001-041)", Presented at the 54th European Renal Association—European Dialysis and Transplant Association Congress; Jun. 3-6, 2017; Madrid, Spain, 1 page.
Scott, C. Ronald, et al., "Identification of infants at risk for developing Fabry, Pompe or Mucopolysaccharidosis-I from newborn blood spots by tandem mass spectrome", Pediatr. Aug. 2013 ; 163(2): 498-503. doi: 10.1016/j.jpeds.2013.01.031.
Serebrinsky, G. , "Late onset variants in Fabry disease: Results in high risk population screenings in Argentina", Molecular Genetics and Metabolism Reports 4 (2015) 19-24.
Sheng, Sen , et al., "Fabry's disease and stroke: Effectiveness of enzyme replacement therapy (ERT) in stroke prevention, a review with meta-analysis", Journal of Clinical Neuroscience 65 (2019) 83-86.
Shin, Sang H., "Prediction of Response of Mutated a-Galactosidase A to a Pharmacological Chaperone", Pharmacogenetics and Genomics, Lippincott Williams & Wilkins, Philadelphia, PA, US, vol. 18, No. 9, Sep. 1, 2008, pp. 773-780.
Sirrs, S. , et al., "Baseline characteristics of patients enrolled in the Canadian Fabry Disease Initiative", Molecular Genetics and Metabolism 99 (2010) 367-373.
Skuban, Nina , et al., "Clinical Outcomes with Migalastat in Patients with Fabry Disease Based on Degree of Renal Impairment: Results from Phase 3 Trials", Nephrology Dialysis Transplantation, vol. 33, 2018 (Supplement 1): i346.
Spada, Marco , et al., "High Incidence of Later-Onset Fabry Disease Revealed by Newborn Screening", The American Journal of Human Genetics, vol. 79, Jul. 2006.
Sunder-Plassmann, Gere , et al., "Migalastat for the treatment of Fabry disease", Expert Opinion on Orphan Drugs, 2018, vol. 6, No. 5, pp. 301-309.
Takahashi, Naoki , "A heterozygous female with Fabry disease due to a novel a-galactosidase A mutation exhibits a unique synaptopodin distribution in vacuolated podocytes", Clin Nephrol. May 2015;83(5):301-8. doi: 10.5414/CN108317. PMID: 25295576., Oct. 8, 2014.
Thomas, Alison Sian Buchanan, "Vascular Events in Fabry and Gaucher Disease", Thesis submitted to Cancer Institute for the degree of MD (Res) (2014).
Tsukimura, Takahiro , et al., "Plasma mutant $\alpha$-galactosidase A protein and globotriaosylsphingosine level in Fabry disease", Molecular Genetics and Metabolism Reports 1 (2014) 288-298.
Tuttolomondo, Antonino , et al., "Novel alpha-galactosidase A mutation in a female with recurrent strokes", Clinical Biochemistry 45 (2012) 1525-1530.
Umeda, Toshiko , et al., "Identification of a novel GLA mutation (F69 L) in a Japanese patient with late-onset Fabry disease", Human Genome Variation (2015) 2, 15044; doi:10.1038/hgv.2015.44.
Van Der Tol, Linda, et al., "In Patients with an a-Galactosidase A Variant, Small Nerve Fibre Assessment Cannot Confirm a Diagnosis of Fabry Disease", JIMD Reports DOI 10.1007/8904_2015_503, Nov. 14, 2015.
Vedder, Anouk C., et al., "Treatment of Fabry Disease: Outcome of a Comparative Trial with Agalsidase Alfa or Beta at a Dose of 0.2 mg/kg", PLoS ONE 2(7): e598. doi:10.1371/journal.pone.0000598 (2007).
Williams, Hadis , et al., "Effects of Long-Term Migalastat Treatment on Renal Function by Baseline Proteinuria in Patients (PTS) with Fabry Disease", Nephrology Dialysis Transplantation, vol. 33, 2018 (Supplement 1): i346-i348.
Wu, Yi Shuan, et al., "Migalastat Tissue Distribution: Extrapolation From Mice to Humans Using Pharmacokinetic Modeling and Comparison With Agalsidase Beta Tissue Distribution in Mice", Clinical Pharmacology in Drug Development 2021, 10(9) 1075-1088.
Garman, Scott C. "Structure-function relationships in a-galactosidase A", Acta Paediatrica 2007, 96, pp. 6-16.
FDA label for Galafold, Aug. 10, 2018, accessible via https://www.accessdata.fda.gov/scripts/cder/daf/index.cfm.
Press Release "Amicus Therapeutics Announces European Commission Approval for GalafoldTM (Migalastat) in Patients with Fabry Disease in European Union", dated May 31, 2016.
Press Release "Amicus Therapeutics Launches Galafold® (Migalastat) for Fabry Disease in Japan", dated May 30, 2018.
Press Release "Amicus Therapeutics Launches GalafoldTM (Migalastat) for Treatment of Fabry Disease in Spain", dated Jan. 17, 2018.
Press Release "Amicus Therapeutics Launches GalafoldTM (Migalastat) for Treatment of Fabry Disease in the United Kingdom", dated Feb. 27, 2017.
Canadian Agency for Drugs and Technologies in Health's Common Drug Review for migalastat (GalafoldTM), Feb. 2018.
"Fabry mutants list", http://fabry-database.org/mutants/, accessed Jan. 24, 2023.
"Study of the Effects of Oral AT1001 (Migalastat Hydrochloride) in Patients With Fabry Disease", ClinicalTrials.gov Archive, Dec. 2010, as of Mar. 31, 2016, http://clinicaltrials.gov/ct2/history/NCR00925301?V_55.
Riera, C. et al., "Table S3. List of mutations and their reference." Dec. 2014, 3 pages, retrieved from the internet: https://www.researchgate.net/publication/269110502_TableS3 [retrieved Nov. 21, 2022].
Flanagan, et al., "The pharmacological chaperone 1-deoxynojirimycin increases the activity and lysosomal trafficking of multiple mutant forms of acid alpha-glucosidase", Human Mutation, vol. 30, Issue 12, Published Nov. 22, 2009, 1683-1692.
Linthorst, et al., "a-Galactosidase A deficiency in Dutch patients on dialysis: a critical appraisal of screening for Fabry disease", Nephrol Dial Transplant (2003) 18: 1581-1584.
Savostyanov, et al., J Inherit Metab Dis (2015) 38 (Suppl 1):S35-S378.
Winchester, et al., "Biochemical and genetic diagnosis of Fabry disease" in Mehta's "Fabry Disease: Perspectives from 5 Years of

(56) References Cited

OTHER PUBLICATIONS

FOS", 2006, including full Figure 1, accessed via https://www.ncbi.nlm.nih.gov/books/NBK11601/ on May 10, 2022.

* cited by examiner

```
ccttctgtaggggcagagaggttctacttcattactgcgtctcctgggaaggccatcag      60
gactgctggctaaagtgggaaccaggactctttgtgagttaagaatttgtgtatttatat    120
gtgtgttatacacatttttaaaaaactgtaacgacatcaggttgagcagtcgtctccgg     180
gtggtgaattatgtgtatttttaaattttatactatattgttatttttcaaatgttcgaa    240
attgaatatgtagattgttgttatcagcagaaaaataaacattattcaaatactctattc    300
agtaaagtaatttattgggcgcctttgtcaagcacgcatttgcctagatgtgactctaca    360
gataaaattcacttggggcctccccttacagacaatcaggcagtggagactgagtgcctg    420
aatggatagaccagcactcagaccactattttcagtatctgtttttcttaactcagggcc    480
gtggttttcaaacgtttttcgccttacggtcacccttagggtcccccgagaccggcccag    540
acagacagatatacaaaaacacatacacagtcatgagcgtccaccatttccccaccaggc    600
gcagcacaggcggcttcccggcactgagatgggggggaggagggagagagcgcgaggggg    660
gaggggaaagcagagaacgaaagaggcggaggcggcccccgaaccccgctctggtcttca    720
tcatcaccaccccctgggtccccagttcccacccacacaccaacctctaacgataccgggt   780
aattttcctccttcttccctcaaacggctatagcgagacggtagacgacgaccagaacta    840
cttctgctcacgtaagcgagtaatcacgtgagcgcctacgtcatgtgagatctcggtcac    900
gtgagcaactctcggcttaaactcgggatcactaaggtgccgcacttccttctggtatgg    960
aaatagggcgggtcaatatcaagaaaggaagagggtgattggttagcggaacgtcttacg    1020
tgactgattattggtctacctctggggataaccgtcccagttgccagagaaacaataacg    1080
tcattatttaataagtcatcggtgattggtccgcccctgaggttaatcttaaaagcccag    1140
gttacccgcggaaatttatgctgtccggtcaccgtgacaatgcagctgaggaacccagaa    1200
ctacatctgggctgcgcgcttgcgcttcgcttcctggccctcgtttcctgggacatccct    1260
ggggctagagcactggacaatggattggcaaggacgcctaccatgggctggctgcactgg    1320
gagcgcttcatgtgcaaccttgactgccaggaagagccagattcctgcatcaggtatcag    1380
atattgggtactcccttccctttgcttttccatgtgtttgggtgtgtttggggaactgga    1440
gagtctcaacgggaacagttgagcccgagggagagctcccccacccgactctgctgctgc    1500
tttttatccccagcaaactgtcccgaatcaggactagccctaaactttctctgtgtgac     1560
ctttcctgggatgggagtccggccagcggcccctgtttctttctctctctctctctctct    1620
cgttctccttctctttctctttctcttctttcctctctctttctctctctccctgcccgg    1680
ttctcttttttcactgctccttgcagagcagggccaccccataggcagtgtgcccaaagt    1740
agccctgcccggttctattcagacccttcttgtgaacttctgctcttcctctgccgggtg    1800
ctaaccgttagaacatctagggtgggtaggaggaatggggaactaagattcgtgccattt    1860
tttctccttttggggtcgtggatttctcggcagtatctcgagggagttagagagaccata    1920
aggtcgctgagatctctcccacctcgcccatgagcgtggcatcaggctggaaggttgaca    1980
tggaggaactttatacatttacacctttgcgtgagggttgaggctggattagataggtat    2040
tgaacatatctgaccctcacaatccttatctgtaaattgggattacaacctttttaatttc   2100
agggagctgacaaaaaaaatctgaaaaatagttcttatctcacacaggtgagttttcaag    2160
gagataacctatttaaagtacatagcacagcgcttgaccattcaactgcgcttacagagc    2220
aaatgttcaatgggaaaatgaatgtaaatctacaaatctgaatgaatatgtgtattttc     2280
tggagagaggatatttacctttcttcaaattctcaaagggctctgtgatttaaaaaaggt    2340
taggaatcactgatagatgttggtaaaaggtggcagtcacagtacatttctgtgtccata    2400
agttattcctatgaatatctttatagataaagtcaggatgttggtcagacatcacagaag    2460
aaattggccttgtaagtttcatgtgaccctgtggtacagtatgtgtggcaattttgccca    2520
tcacggattttttttattggtatttgcatctgattataaaactaatgcatgatcattgc     2580
aaaaaatgtagataaagaagagcaaaatgaaaataaagatttccccccaccgttccacca    2640
cccagaaataatcatggtttaaatgttaatatacaaccttacaattgttttctatataaa    2700
tgaaaacatagatttctttatttcattattttccataaaaaatggatcatgtttatgtca    2760
tgtttggctaatggcaagaccctggcacccagtctgggctcaaattctgcctcattgtta    2820
cttagccctgtgacattgggtaaattacactttttttttttttttttttttgagacgggg    2880
```

FIG. 1A

```
tctcgctctgtcgcccaggctggagtgcagtggcacgatctcggctcactgcaagtccgc    2940
ctcctgggttcacgccattcttctgcctcagcctcccgagtagctgggactacaggcgcc    3000
tgccaccacgcctggctcttttttttttttttttttttttttagtacagacggggtttcac   3060
catgttagccagggtggtctcaatctcctgacctcgtgattcgcccgcctcagcctccca    3120
aagtgctggtgtgagccaccgtgcccagccttacttttttttttttgagaggggtctcact   3180
ctgtcacccaggttggagtgcagtggcgcgatctctgctcagtgcaaactccacctcccg    3240
ggtttaagcagttctcctgtcgtagtctcctgagtagctgggattacaggcacaccacca    3300
cggccagctaattttttgtattttcagtagagacgggtttcaccatgttgcccaagctggt   3360
ctcgaactcctggcctcaagtgatctgcccgccttggcctcccagagtgctgggattaca    3420
ggtgtgagccaccgcacccggcctctttttttctttttttagtctatcataccttgcaaata  3480
cagtggttcttcctatgtgttggttttgatatttatgtaatcaaacacatcagtttttcc    3540
tttctgatttctgactttggggtcatgctgagaaagtcctttcctacctgaagataatac    3600
agtatatacgtttcttactagtattttttgtggattttttaaaatatttaaatctttagtcc  3660
atctgaacttgttcttctatcagaaatgccacatttaataaataataagtcccatggtat    3720
cagatggctggaaggacctctttcgaaactttgtttaattccattaatctgtgtattctt    3780
attctaatgctaatagttccactagcttcctttatcttttttttctttttttttttttttt   3840
ttttgagctggagtttcgctcttgttgcccaggctggagtacaatgtcacgatctcggtt    3900
caccgcaacctccgcctcccaggttcaagcaattctcctgcctcatcctcgcgagtagct    3960
ggaattacaggcatgcgccaccacgcctagctatttttgtatttttagtagagatggggtt   4020
tctccatgttggtcaggctggtctcaaactcccagcctcaggtgatctgcctgcctcggc    4080
ctcccaaaatgctgttattacaggcgtgagccaccacgcccagccttcatcttttaatga    4140
atgtacatgtatgtaatcttttaggtgaactttttgtaatgttgtgccaagttccttaaa    4200
aagccctttttggaagctgggcaggtggccacgcctgtaatcccagcatttgggagtctg    4260
aggcaggtggatcacttgaggccaggagttcaagactagcctagccaaaatgcaaaaccc    4320
tgtctctactaaagatacaaaaattagccggatgcgatggcacatgcctgtaatctcagc    4380
tactcgggaggctgaggtagaagaatcgcttgaaccggggaggcagaggttgcagtgagc    4440
aagatggcgccactgcactccagcctgggtgacagagggagactccatctcaaaaaaaaaa   4500
aaaaaaaaaaaagataaaaaggaaacctaagtactcttgggctttgttaaggattttgtt    4560
aaatatacaaaggattgcagggaaaattaacttatttttaatattgagtatgcttatcca    4620
agagcaaaataatatttctccatttattcaaatcatttaggagcatcatagttttaacat    4680
atgggccttgcacgtatcttaaatttatctctaggcattttaggttgttcagttgttctt    4740
gtgaatgggatctttttctccaaataggattattgttgatatctgttgattatgttaact    4800
ttgtagtttctgactttactgaactgtcttcttagatctaatactcttttcaatttcatc    4860
atatatttctcattcctattttgtttggggtttttagggcgggaatattaacgggataag    4920
agagacaaaagaaaatctggaaaaacaattcattttaccttacattgcttgtgattacta    4980
ccacactattactgggttggaaaaaattgtgaaatcccaaggtgcctaataaatgggagg    5040
tacctaagtgttcatttaatgaattgtaatgattattggaatttctctttcagtgagaag    5100
ctcttcatggagatggcagagctcatggtctcagaaggctggaaggatgcaggttatgag    5160
tacctctgcattgatgactgttggatggctccccaaagagattcagaaggcagacttcag    5220
gcagaccctcagcgctttcctcatgggattcgccagctagctaattatgtgagtttatag    5280
ataatgttcttgttcattcagaggactgtaagcacttctgtacagaagcttgtttagaaa    5340
cagccctcatggccgggcgtggtggctcacgctgtaatcccaacactttgggaggccgag    5400
gcgggtggatcacctgaggtcaagagttcaagaccagcctggccaacatggtgaaacccc    5460
aactctattaaaagtacaaaaaattagctgggcatggtggtgaacgcctgtaaccccagc    5520
tacttgggaggctgaggcaggagaatcgcttgaacccaggaggtggaagtttcagtgagc    5580
tgagatcacgccattgcactctagcctgggcaacaaaagagaaactccatctcaaaaaaa    5640
aaaacaaggaaaaaaagaaacagccctcatgacacttagaaagtagaatagctggctgtt    5700
atctgaacattgaattgtaaggcttatcaggtggactttgcattccatcagcagacaatt    5760
```

FIG. 1B

```
ttttttttttttttttttttgagatggagtctcattctgtctcccaggctggagggcagtg      5820
gtgcgatctcggctcactgcaagctccacctcctgggttcatgccattctcctgcctcag      5880
cctcccaagtagctgggaccacaggcacccgccaccatgcccagttaatttttgtattt       5940
ttagtagagacggggtttcaccatgttagccaagatggtctcgatctcctgacctcgtga      6000
tccgcccacctcggcctcccaaagtgctgggattacaggcatgagccaccgcgcctagcc      6060
tacaaatgttttgtaatagctcttgaggcccatcttggagttctcctttttgctaaaacca      6120
ctgaactctctaggaggaaaaaggaacttggttcttgacatatgtgtgcatgtatttcca      6180
tataacctttaggaagctattgcaatggtactataaactagaattttagaagatagaagg      6240
aaaatattctggagatcattgaagagaaatggagtccaacactagttaaagatgatgaag      6300
acagattttttttttttgacggagtctcgctctgtcgcccaggctggagtgcagtggcaca     6360
atctcagctcactgcaaccctccacctcttgggttcaagtgattctcctgcctcagcctc      6420
ccaagtagctgggactacaggcgcacaccaccacgcccggctaatttttgtatttttagt      6480
agagacaaggtttcaccatattcgccaggctggtctcgaactcctgaccttgtaatccgc      6540
ccaccttggcctcccaaagtgctgggattacaggcatgagccaccacgcccggccgatga      6600
agacagattttattcagtactaccacagtagaggaaagagccaagttcaattccaaatac      6660
aacaaagacaggtggagatttatagccaatgagcagattgaggggtcagtggatggaat      6720
atttaagaagacatcaagggtagggagcttcttgctaaagcttcatgtacttaaacaaga      6780
agggtgggggatgagggaaattgatcagatatcaatggtggcagtattgacttagcagga      6840
ttcttgctaagaggtcttgctaggacagacataggaagccaaggtggaggtctagtcgaa      6900
aagaaggctcatcagagaagtctaactaaagtttggtcaagaagagtctttgtcaaggta      6960
aatctatcatttccctcaaaaggtaattttcaggatcccatcaggaagattagcatggct      7020
gctagctttctcctcagttctgggctatagctcacatgcctagtttgaactagctcagca      7080
gaactggggatttattctttgtcttccaacaaactcatctggatgattttggggtttg        7140
tggggaaaagcccccaatacctggtgaagtaaccttgtctcttcccccagcctggaatgg      7200
ttctctctttctgctacctcacgattgtgcttctacaatggtgactcttttcctccctct      7260
catttcaggttcacagcaaaggactgaagctagggatttatgcagatgttggaaataaaa      7320
cctgcgcaggcttccctgggagttttggatactacgacattgatgcccagacctttgctg      7380
actggggagtagatctgctaaaatttgatggttgttactgtgacagtttggaaaatttgg      7440
cagatggtaatgtttcattccagagatttagccacaaaggaaagaactttgaggccatgg      7500
tagctgagccaaagaaccaatcttcagaattttaaataccctgtcacaatactggaaata      7560
attattctccatgtgccagagctcccatctcttctctttcagttcattaattaattaatt      7620
aattcatgtaaaatccatgcatacctaaccatagctaatattgtgcacttataattcaag      7680
agggctctaagagttaattagtaattgtaactctctataacatcatttaggggagtccag      7740
gttgtcaatcggtcacagagaaagaagcatcttcattcctgcctttcctcaatatacaca      7800
ccatctctgcactacttcctcagaacaatcccagcagtctgggaggtactttacacaatt      7860
taagcacagagcaactgcctgtccctgctgctagtttaaacatgaaccttccaggtagcc      7920
tcttcttaaaatatacagccccagctgggcatgatggctcatgcctgtaatcctagcact      7980
ttgggaggctgaggcgggtggattacttgaggtcaggagttcgagaccaccctggccaac      8040
atggtgaaaccccatctctagtaaaaatacaaaaattagctgactttggtggcacatgcc      8100
tgtaatcccagctacttgggaagctgagacagaagagtcacttgaacctgggaaacagag      8160
gttgcagtgagccaagatcgcaccactgcactccaccctggatgacagactgaaccccat      8220
ctcaaaaaattaaaataaaataaaataaaataactatatatatagccccagctggaaatt      8280
catttctttcccttattttacccattgttttctcatacaggttataagcacatgtccttg      8340
gccctgaataggactggcagaagcattgtgtactcctgtgagtggcctctttatatgtgg      8400
ccctttcaaaggtgagatagtgagcccagaatccaatagaactgtactgatagatagaa       8460
cttgacaacaaaggaaaccaaggtctccttcaaagtccaacgttacttactatcatccta      8520
ccatctctcccaggttccaaccacttctcaccatccccactgctgtaattatagcctaag      8580
ctaccatcacctggaaagtcatccttgtgtcttcccctttatttcaccattcatgtcctg      8640
```

FIG. 1C tctatcaacagtccttccaccagtatctctaaaatatctcctgaatcagcccacttcctt 8700
ccatcttcactacatgcaccctggccttccaagctactatcggctctcaaccagactgct 8760
gggaccacctgatctctctgcttccactctgtctcaacccccatctattttccaagcagc 8820
actagagttatcatattaaaatgtaaatatcagtttttttttaaagaaaaaaaccctga 8880
gacttaacagagttataaaaaatataaatgtcatcatcagttccctgcttaaaacccttta 8940
actcgcttccaattgcacttggaatgaaaccaaactgcactgatccagcccttgcctgcc 9000
tccccaaagtccaaggggtcatggctctttccctggctacactggtttctttctgtccc 9060
tcaacactgcaagcctattgctgccccagggcctttacacttgctttttttctgcctaga 9120
acagttcttccccaaagattttaaagggccgggctccttaacattgaagtcgcagacca 9180
aacgccacatatgcagacagttcttctctaactactttaaaatagccctctgtccattca 9240
ttcttcatcacattaacctgtttaatttcttctcagagctccacactatttggaagtat 9300
ttgttgacttgttaccatgtctccccactagagtgtaagtttcatgagggcagggacctt 9360
gtctgactttgactgtatctctcgcatatggttaagtgttaaatagttatttatggaatg 9420
aatccctattattccctcattatctctgcaaaatagtctttttttctcaacatcttaaacc 9480
tgatatcccacctgcctatctacaaacttttttttttgcgacagagtctcactgtcaccca 9540
ggctagagtgcagtggcgccatctcggctcactgcaacctccgcctcccgggtttaagcg 9600
attctcttgcctcagcctcccagtagctgggattataggcgtgcgctaccacatctggct 9660
aatttttgtatttttagtagagatggtttcaccatgttggccaggcttgtctcgaactcc 9720
tgacctcagatgatccacctgcctcggcctcccaaagtgctgggattacaggcatgagcc 9780
accgtgcccagcctctacaaactttttattccattaacaaactatatgctgggatttaag 9840
ttttcttaatacttgatggagtcctatgtaattttcgagcttttaattttactaagacca 9900
ttttagttctgattatagaagtaaattaactttaagggatttcaagttatatggcctact 9960
tctgaagcaaacttcttacagtgaaaattcattataagggtttagacctccttatggaga 10020
cgttcaatctgtaaactcaagagaaggctacaagtgcctcctttaaactgttttcatctc 10080
acaaggatgttagtagaaagtaaacagaagagtcatatctgttttcacagcccaattata 10140
cagaaatccgacagtactgcaatcactggcgaaattttgctgacattgatgattcctgga 10200
aaagtataaagagtatcttggactggacatcttttaaccaggagagaattgttgatgttg 10260
ctggaccaggggggttggaatgacccagatatggtaaaaacttgagccctccttgttcaag 10320
accctgcggtaggcttgtttcctattttgacattcaaggtaaatacaggtaaagttcctg 10380
ggaggaggctttatgtgagagtacttagagcaggatgctgtggaaagtggtttctccata 10440
tgggtcatctaggtaactttaagaatgtttcctcctctcttgtttgaattatttcattct 10500
ttttctcagttagtgattggcaactttggcctcagctggaatcagcaagtaactcagatg 10560
gccctctgggctatcatggctgctcctttattcatgtctaatgacctccgacacatcagc 10620
cctcaagccaaagctctccttcaggataaggacgtaattgccatcaatcaggacccttg 10680
ggcaagcaagggtaccagcttagacaggtaaataagagtatatattttaagatggcttta 10740
tatacccaataccaactttgtcttgggcctaaatctatttttttcccttgctcttgatgt 10800
tactatcagtaataaagcttcttgctagaaacattactttatttccaaaataatgctaca 10860
ggatcattttaattttcctacaagtgcttgatagttctgacattaagaatgaatgccaa 10920
actaacagggccacttatcactagttgctaagcaaccacactttcttggtttttcaggga 10980
gacaactttgaagtgtgggaacgacctctctcaggcttagcctgggctgtagctatgata 11040
aaccggcaggagattggtggacctcgctcttataccatcgcagttgcttccctgggtaaa 11100
ggagtggcctgtaatcctgcctgcttcatcacacagctcctccctgtgaaaaggaagcta 11160
gggttctatgaatggacttcaaggttaagaagtcacataaatcccacaggcactgttttg 11220
cttcagctagaaaatacaatgcagatgtcattaaaagacttactttaaaatgtttatttt 11280
attgccaactactacttcctgtccacctttttctccattcactttaaaagctcaaggcta 11340
ggtggctcatgcctgtaatcccagcactttgggaggctgaggcgggcagatcacctgagg 11400
tcgggactttgagacccgcctggacaacatggtgaaaccccatttctaataaaaatataa 11460
aaattagccaggtgtggtggcgcacctgtggtcccagctactctgggggctgaggcatga 11520

FIG. 1D

```
gaatcgcttgaacccgggagtggaggttgcattgagctgagatcatgccacctcactcca      11580
gcctgggcaacaaagattccatctcaaaaaaaaaaaaaaagccaggcacagtggctcatg      11640
cctggaatcccagcacttttggaagctgaggcaggcagatcacttgaggttaggatttca      11700
agaccagcctggctaacatagtaaagccctgtctctactaaaaatacaaaaattagccag      11760
gtatggtggcgagcttctgtagccccagctactcaggagactgaggcaggagaatcactt      11820
gaacccgggaagtgggggggtgcagtgacccaagatcacgccactgcattccagcctggg      11880
caacagagcaagactccatctcaaaaaaaaaaagttctatttccttgaataaattttccg      11940
aagtttaaactttaggaataaaactattaaacccgtatttactcatccagatacccaccc      12000
cccttgttgagattctctcccaattatcaaaatgtgtagcatatttaactaccaagagct      12060
aaacatcattaagactgaaatgtattaagaaggatgtataggccaggcacggtgtctcac      12120
gcctgtaatcccaacactttgggaggccaagtcgggcggatcacgaggtcaggagatgga      12180
gaccatcctggccaacatggtgaaaccccctctctactaaaaatacaaaaattagccagg      12240
caggtggcaggcacctgtaatcccagctactccagaggctgaggcaggacaatcacttga      12300
acctgggaggcagaggctgcagtgagctgaggttgtaccaattgcactccagcctaggta      12360
acgagcaacactccatctcaaaaaaagaaaaaaaaaaagatgtataatttggaactgtta      12420
agaggcattttaaaga                                                  12436
```

FIG. 1E

```
MQLRNPELHL GCALALRFLA LVSWDIPGAR ALDNGLARTP TMGWLHWERF MCNLDCQEEP   60
DSCISEKLFM EMAELMVSEG WKDAGYEYLC IDDCWMAPQR DSEGRLQADP QRFPHGIRQL  120
ANYVHSKGLK LGIYADVGNK TCAGFPGSFG YYDIDAQTFA DWGVDLLKFD GCYCDSLENL  180
ADGYKHMSLA LNRTGRSIVY SCEWPLYMWP FQKPNYTEIR QYCNHWRNFA DIDDSWKSIK  240
SILDWTSFNQ ERIVDVAGPG GWNDPDMLVI GNFGLSWNQQ VTQMALWAIM AAPLFMSNDL  300
RHISPQAKAL LQDKDVIAIN QDPLGKQGYQ LRQGDNFEVW ERPLSGLAWA VAMINRQEIG  360
GPRSYTIAVA SLGKGVACNP ACFITQLLPV KRKLGFYEWT SRLRSHINPT GTVLLQLENT  420
MQMSLKDLL                                                          429
```

FIG. 2

```
atgcagctgaggaatcccgagctccacctgggctgtgctctggctctgcggttcctggccctc
gtgtcctgggacatccctggcgctagggccctcgataacggactggcccggacccccacaatg
ggatggctccactgggaaaggttcatgtgcaatctggactgtcaggaggaacccgactcctgc
atcagcgaaaagctcttcatggagatggccgagctgatggtgagcgagggctggaaggacgcc
ggctacgagtatctgtgcatcgatgactgctggatggcccctcaaagggactccgaaggcagg
ctgcaggctgatccccaaaggtttccccacggaatccggcagctcgccaactacgtgcattcc
aagggcctcaagctcggcatctacgccgacgtgggcaacaaaacatgcgccggattccccggc
agcttcggctactacgacatcgacgcccagacattcgctgattggggagtggacctgctgaag
ttcgacggctgttactgcgattccctggaaaacctggccgacggctacaaacacatgtccctc
gccctgaaccggacaggcaggtccatcgtgtacagctgcgagtggcccctgtacatgtggcct
ttccagaagcccaactacacagagatcaggcagtactgcaaccactggaggaacttcgctgac
atcgacgactcctggaagagcatcaagagcatcctggactggaccagcttcaaccaggagagg
atcgtggacgtggctggacccggaggctggaacgaccccgatatgctggtgattggcaacttc
ggactgagctggaaccagcaggtgacccagatggccctgtgggccattatggccgctcccctg
ttcatgtccaacgacctgaggcacatcagcccccaggccaaggctctgctgcaggacaaggat
gtgatcgccatcaaccaggacccccctgggcaagcagggctaccagctgaggcaaggagataac
ttcgaggtgtgggagaggcccctgtccggactggcttgggccgtggccatgatcaatcggcag
gagatcggcggaccccggtcctacaccattgctgtggccagcctgggaaaaggagtcgcctgc
aaccccgcctgcttcattacccagctgctccccgtgaagcggaagctgggcttctatgagtgg
accagcaggctgaggtcccatatcaatcctaccggcaccgtcctcctccagctcgagaatacc
atgcagatgagcctcaaggatctgctgtga
```

FIG. 3

SEQUENCE LISTING

```
<160> NUMBER OF SEQ ID NOS: 3

<210> SEQ ID NO 1
<211> LENGTH: 12436
<212> TYPE: DNA
<213> ORGANISM: Homo sapiens
```

-continued

<400> SEQUENCE: 1

```
cccttctgta ggggcagaga ggttctactt cattactgcg tctcctggga aggccatcag     60
gactgctggc taaagtggga accaggactc tttgtgagtt aagaatttgt gtatttatat    120
gtgtgttata cacatttttt aaaaaactgt aacgacatca ggttgagcag tcgtctccgg    180
gtggtgaatt atgtgtattt ttaaatttta tactatattg ttatttttca aatgttcgaa    240
attgaatatg tagattgttg ttatcagcag aaaaataaac attattcaaa tactctattc    300
agtaaagtaa tttattgggc gcctttgtca agcacgcatt tgcctagatg tgactctaca    360
gataaaattc acttggggcc tccccttaca gacaatcagg cagtggagac tgagtgcctg    420
aatggataga ccagcactca gaccactatt ttcagtatct gtttttctta actcagggcc    480
gtggttttca aacgtttttc gccttacggt cacccttagg gtcccccgag accggcccag    540
acagacagat atacaaaaac acatacacag tcatgagcgt ccaccatttc cccaccaggc    600
gcagcacagg cggcttcccg gcactgagat gggggggagg agggagagag cgcgaggggg    660
gaggggaaag cagagaacga aagaggcgga ggcggccccc gaaccccgct ctggtcttca    720
tcatcaccac ccctgggtcc ccagttccca cccacacacc aacctctaac gataccgggt    780
aattttcctc cttcttccct caaacggcta tagcgagacg gtagacgacg accagaacta    840
cttctgctca cgtaagcgag taatcacgtg agcgcctacg tcatgtgaga tctcggtcac    900
gtgagcaact ctcggcttaa actcgggatc actaaggtgc cgcacttcct tctggtatgg    960
aaatagggcg ggtcaatatc aagaaaggaa gagggtgatt ggttagcgga acgtcttacg   1020
tgactgatta ttggtctacc tctggggata accgtcccag ttgccagaga aacaataacg   1080
tcattattta ataagtcatc ggtgattggt ccgcccctga ggttaatctt aaaagcccag   1140
gttacccgcg gaaatttatg ctgtccggtc accgtgacaa tgcagctgag gaacccagaa   1200
ctacatctgg gctgcgcgct tgcgcttcgc ttcctggccc tcgtttcctg ggacatccct   1260
ggggctagag cactggacaa tggattggca aggacgccta ccatgggctg gctgcactgg   1320
gagcgcttca tgtgcaacct tgactgccag gaagagccag attcctgcat caggtatcag   1380
atattgggta ctcccttccc tttgcttttc catgtgtttg ggtgtgtttg gggaactgga   1440
gagtctcaac gggaacagtt gagcccgagg gagagctccc ccacccgact ctgctgctgc   1500
tttttttatcc ccagcaaact gtcccgaatc aggactagcc ctaaactttc tctgtgtgac   1560
ctttcctggg atgggagtcc ggccagcggc ccctgtttct ttctctctct ctctctctct   1620
cgttctcctt ctctttctct ttctcttctt tcctctctct ttctctctct ccctgcccgg   1680
ttctcttttt tcactgctcc ttgcagagca gggccacccc ataggcagtg tgcccaaagt   1740
agccctgccc ggttctattc agacccttct tgtgaacttc tgctcttcct ctgccgggtg   1800
ctaaccgtta gaacatctag ggtgggtagg aggaatgggg aactaagatt cgtgccattt   1860
tttctccttt tggggtcgtg gatttctcgg cagtatctcg agggagttag agagaccata   1920
aggtcgctga gatctctccc acctcgccca tgagcgtggc atcaggctgg aaggttgaca   1980
tggaggaact ttatacattt acacctttgc gtgagggttg aggctggatt agataggtat   2040
tgaacatatc tgaccctcac aatccttatc tgtaaattgg gattacaacc ttttaatttc   2100
agggagctga caaaaaaaat ctgaaaaata gttcttatct cacacaggtg agttttcaag   2160
gagataacct atttaaagta catagcacag cgcttgacca ttcaactgcg cttacagagc   2220
aaatgttcaa tgggaaaatg aatgtaaatc tacaaatctg aatgaatatg tgtatttttc   2280
tggagagagg atatttacct ttcttcaaat tctcaaaggg ctctgtgatt taaaaaaggt   2340
```

-continued

```
taggaatcac tgatagatgt tggtaaaagg tggcagtcac agtacatttc tgtgtccata   2400
agttattcct atgaatatct ttatagataa agtcaggatg ttggtcagac atcacagaag   2460
aaattggcct tgtaagtttc atgtgaccct gtggtacagt atgtgtggca attttgccca   2520
tcacggattt ttttttattg gtatttgcat ctgattataa aactaatgca tgatcattgc   2580
aaaaaatgta gataaagaag agcaaaatga aaataaagat ttccccccac cgttccacca   2640
cccagaaata atcatggttt aaatgttaat atacaacctt acaattgttt tctatataaa   2700
tgaaaacata gatttcttta tttcattatt ttccataaaa aatggatcat gtttatgtca   2760
tgtttggcta atggcaagac cctggcaccc agtctgggct caaattctgc ctcattgtta   2820
cttagccctg tgacattggg taaattacac tttttttttt tttttttttt tgagacgggg   2880
tctcgctctg tcgcccaggc tggagtgcag tggcacgatc tcggctcact gcaagtccgc   2940
ctcctgggtt cacgccattc ttctgcctca gcctcccgag tagctgggac tacaggcgcc   3000
tgccaccacg cctggctctt tttttttttt tttttttttt tagtacagac ggggtttcac   3060
catgttagcc agggtggtct caatctcctg acctcgtgat tcgcccgcct cagcctccca   3120
aagtgctggt gtgagccacc gtgcccagcc ttactttttt ttttgagagg gggtctcact   3180
ctgtcaccca ggttggagtg cagtggcgcg atctctgctc agtgcaaact ccacctcccg   3240
ggtttaagca gttctcctgt cgtagtctcc tgagtagctg ggattacagg cacaccacca   3300
cggccagcta atttttgtat tttcagtaga gacgggtttc accatgttgc ccaagctggt   3360
ctcgaactcc tggcctcaag tgatctgccc gccttggcct cccagagtgc tgggattaca   3420
ggtgtgagcc accgcacccg gcctcttttt tctttttttag tctatcatac cttgcaaata   3480
cagtggttct tcctatgtgt tggttttgat atttatgtaa tcaaacacat cagtttttcc   3540
tttctgattt ctgactttgg ggtcatgctg agaaagtcct ttcctacctg aagataatac   3600
agtatatacg tttcttacta gtatttttgt ggatttttaa aatatttaaa tctttagtcc   3660
atctgaactt gttcttctat cagaaatgcc acatttaata aataataagt cccatggtat   3720
cagatggctg gaaggacctc tttcgaaact ttgtttaatt ccattaatct gtgtattctt   3780
attctaatgc taatagttcc acactagctt cctttatctt ttttttcttt tttttttttt   3840
ttttgagctg gagtttcgct cttgttgccc aggctggagt acaatgtcac gatctcggtt   3900
caccgcaacc tccgcctccc aggttcaagc aattctcctg cctcatcctc gcgagtagct   3960
ggaattacag gcatgcgcca ccacgcctag ctattttgta tttttagtag agatggggtt   4020
tctccatgtt ggtcaggctg gtctcaaact cccagcctca ggtgatctgc ctgcctcggc   4080
ctcccaaaat gctgttatta caggcgtgag ccaccacgcc cagccttcat cttttaatga   4140
atgtacatgt atgtaatctt ttaggtgaac tttttgtaat gttgtgccaa gttccttaaa   4200
aagccctttt ggaagctggg caggtggcca cgcctgtaat cccagcattt tgggagtctg   4260
aggcaggtgg atcacttgag gccaggagtt caagactagc ctagccaaaa tgcaaaaccc   4320
tgtctctact aaagatacaa aaattagccg gatgcgatgg cacatgcctg taatctcagc   4380
tactcgggag gctgaggtag aagaatcgct tgaaccgggg aggcagaggt tgcagtgagc   4440
aagatggcgc cactgcactc cagcctgggt gacagaggga gactccatct caaaaaaaaa   4500
aaaaaaaaaa aagataaaaa ggaaacctaa gtactcttgg gctttgttaa ggattttgtt   4560
aaatatacaa aggattgcag ggaaaattaa cttattttta atattgagta tgcttatcca   4620
agagcaaaat aatatttctc catttattca aatcatttag gagcatcata gttttaacat   4680
```

-continued

```
atgggccttg cacgtatctt aaatttatct ctaggcattt taggttgttc agttgttctt   4740
gtgaatggga tctttttctc caaataggat tattgttgat atctgttgat tatgttaact   4800
ttgtagtttc tgactttact gaactgtctt cttagatcta atactctttt caatttcatc   4860
atatatttct cattcctatt ttgtttgggg tttttagggc gggaatatta acgggataag   4920
agagacaaaa gaaaatctgg aaaaacaatt cattttacct tacattgctt gtgattacta   4980
ccacactatt actgggttgg aaaaaattgt gaaatcccaa ggtgcctaat aaatgggagg   5040
tacctaagtg ttcatttaat gaattgtaat gattattgga atttctcttt cagtgagaag   5100
ctcttcatgg agatggcaga gctcatggtc tcagaaggct ggaaggatgc aggttatgag   5160
tacctctgca ttgatgactg ttggatggct ccccaaagag attcagaagg cagacttcag   5220
gcagaccctc agcgctttcc tcatgggatt cgccagctag ctaattatgt gagtttatag   5280
ataatgttct tgttcattca gaggactgta agcacttctg tacagaagct tgtttagaaa   5340
cagccctcat ggccgggcgt ggtggctcac gctgtaatcc caacactttg ggaggccgag   5400
gcgggtggat cacctgaggt caagagttca agaccagcct ggccaacatg gtgaaacccc   5460
aactctatta aaagtacaaa aaattagctg ggcatggtgg tgaacgcctg taaccccagc   5520
tacttgggag gctgaggcag gagaatcgct tgaacccagg aggtggaagt ttcagtgagc   5580
tgagatcacg ccattgcact ctagcctggg caacaaaaga gaaactccat ctcaaaaaaa   5640
aaaacaagga aaaaaagaaa cagccctcat gacacttaga aagtagaata gctggctgtt   5700
atctgaacat tgaattgtaa ggcttatcag gtggactttg cattccatca gcagacaatt   5760
tttttttttt tttttttttg agatggagtc tcattctgtc tcccaggctg gagggcagtg   5820
gtgcgatctc ggctcactgc aagctccacc tcctgggttc atgccattct cctgcctcag   5880
cctcccaagt agctgggacc acaggcaccc gccaccatgc ccagttaatt ttttgtattt   5940
ttagtagaga cggggtttca ccatgttagc caagatggtc tcgatctcct gacctcgtga   6000
tccgcccacc tcggcctccc aaagtgctgg gattacaggc atgagccacc gcgcctagcc   6060
tacaaatgtt ttgtaatagc tcttgaggcc catcttggag ttctcctttt gctaaaacca   6120
ctgaactctc taggaggaaa aaggaacttg gttcttgaca tatgtgtgca tgtatttcca   6180
tataaccttt aggaagctat tgcaatggta ctataaacta gaattttaga agatagaagg   6240
aaaatattct ggagatcatt gaagagaaat ggagtccaac actagttaaa gatgatgaag   6300
acagattttt tttttttgacg gagtctcgct ctgtcgccca ggctggagtg cagtggcaca   6360
atctcagctc actgcaaccc tccacctctt gggttcaagt gattctcctg cctcagcctc   6420
ccaagtagct gggactacag gcgcacacca ccacgcccgg ctaatttttg tatttttagt   6480
agagacaagg tttcaccata ttcgccaggc tggtctcgaa ctcctgacct tgtaatccgc   6540
ccaccttggc ctcccaaagt gctgggatta caggcatgag ccaccacgcc cggccgatga   6600
agacagattt tattcagtac taccacagta gaggaaagag ccaagttcaa ttccaaatac   6660
aacaaagaca ggtggagatt tatagccaat gagcagattg agggggtcag tggatggaat   6720
atttaagaag acatcaaggg tagggagctt cttgctaaag cttcatgtac ttaaacaaga   6780
agggtggggg atgagggaaa ttgatcagat atcaatggtg gcagtattga cttagcagga   6840
ttcttgctaa gaggtcttgc taggacagac ataggaagcc aaggtggagg tctagtcgaa   6900
aagaaggctc atcagagaag tctaactaaa gtttggtcaa gaagagtctt tgtcaaggta   6960
aatctatcat ttccctcaaa aggtaatttt caggatccca tcaggaagat tagcatggct   7020
gctagctttc tcctcagttc tgggctatag ctcacatgcc tagtttgaac tagctcagca   7080
```

-continued

```
gaactggggg atttattctt tgtcttccaa caaactcatc tggatgattt tgggggtttg   7140
tggggaaaag cccccaatac ctggtgaagt aaccttgtct cttcccccag cctggaatgg   7200
ttctctcttt ctgctacctc acgattgtgc ttctacaatg gtgactcttt tcctccctct   7260
catttcaggt tcacagcaaa ggactgaagc tagggattta tgcagatgtt ggaaataaaa   7320
cctgcgcagg cttccctggg agttttggat actacgacat tgatgcccag acctttgctg   7380
actggggagt agatctgcta aaatttgatg gttgttactg tgacagtttg gaaaatttgg   7440
cagatggtaa tgtttcattc cagagattta gccacaaagg aaagaacttt gaggccatgg   7500
tagctgagcc aaagaaccaa tcttcagaat tttaaatacc ctgtcacaat actggaaata   7560
attattctcc atgtgccaga gctcccatct cttctctttc agttcattaa ttaattaatt   7620
aattcatgta aaatccatgc atacctaacc atagctaata ttgtgcactt ataattcaag   7680
agggctctaa gagttaatta gtaattgtaa ctctctataa catcatttag gggagtccag   7740
gttgtcaatc ggtcacagag aaagaagcat cttcattcct gcctttcctc aatatacaca   7800
ccatctctgc actacttcct cagaacaatc ccagcagtct gggaggtact ttacacaatt   7860
taagcacaga gcaactgcct gtccctgctg ctagtttaaa catgaacctt ccaggtagcc   7920
tcttcttaaa atatacagcc ccagctgggc atgatggctc atgcctgtaa tcctagcact   7980
ttgggaggct gaggcgggtg gattacttga ggtcaggagt tcgagaccac cctggccaac   8040
atggtgaaac cccatctcta gtaaaaatac aaaaattagc tgactttggt ggcacatgcc   8100
tgtaatccca gctacttggg aagctgagac agaagagtca cttgaacctg ggaaacagag   8160
gttgcagtga gccaagatcg caccactgca ctccaccctg gatgacagac tgaaccccat   8220
ctcaaaaaat taaaataaaa taaaataaaa taactatata tatagcccca gctggaaatt   8280
catttctttc ccttatttta cccattgttt tctcatacag gttataagca catgtccttg   8340
gccctgaata ggactggcag aagcattgtg tactcctgtg agtggcctct ttatatgtgg   8400
ccctttcaaa aggtgagata gtgagcccag aatccaatag aactgtactg atagatagaa   8460
cttgacaaca aaggaaacca aggtctcctt caaagtccaa cgttacttac tatcatccta   8520
ccatctctcc caggttccaa ccacttctca ccatccccac tgctgtaatt atagcctaag   8580
ctaccatcac ctggaaagtc atccttgtgt cttccccttt atttcaccat tcatgtcctg   8640
tctatcaaca gtccttccac cagtatctct aaaatatctc ctgaatcagc ccacttcctt   8700
ccatcttcac tacatgcacc ctggccttcc aagctactat cggctctcaa ccagactgct   8760
gggaccacct gatctctctg cttccactct gtctcaaccc ccatctattt tccaagcagc   8820
actagagtta tcatattaaa atgtaaatat cagttttttt tttaaagaaa aaaaccctga   8880
gacttaacag agttataaaa aatataaatg tcatcatcag ttccctgctt aaaaccctta   8940
actcgcttcc aattgcactt ggaatgaaac caaactgcac tgatccagcc cttgcctgcc   9000
tccccaaagt ccaaggggtc atggctcttt ccctggctac actggtttc tttctgtccc   9060
tcaacactgc aagcctattg ctgccccagg gcctttacac ttgctttttt tctgcctaga   9120
acagttcttc cccaaagatt tttaaagggc cgggctcctt aacattgaag tcgcagacca   9180
aacgccacat atgcagacag ttcttctcta actactttaa aatagccctc tgtccattca   9240
ttcttcatca cattaacctg tttaattttc ttctcagagc tccacactat ttggaagtat   9300
ttgttgactt gttaccatgt ctccccacta gagtgtaagt ttcatgaggg cagggacctt   9360
gtctgacttt gactgtatct ctcgcatatg gttaagtgtt aaatagttat ttatggaatg   9420
```

-continued aatccctatt attccctcat tatctctgca aaatagtctt ttttctcaac atcttaaacc 9480
tgatatccca cctgcctatc tacaaacttt ttttttgcga cagagtctca ctgtcaccca 9540
ggctagagtg cagtggcgcc atctcggctc actgcaacct ccgcctcccg ggtttaagcg 9600
attctcttgc ctcagcctcc cagtagctgg gattataggc gtgcgctacc acatctggct 9660
aatttttgta tttttagtag agatggtttc accatgttgg ccaggcttgt ctcgaactcc 9720
tgacctcaga tgatccacct gcctcggcct cccaaagtgc tgggattaca ggcatgagcc 9780
accgtgccca gcctctacaa actttttatt ccattaacaa actatatgct gggatttaag 9840
ttttcttaat acttgatgga gtcctatgta attttcgagc ttttaatttt actaagacca 9900
ttttagttct gattatagaa gtaaattaac tttaagggat ttcaagttat atggcctact 9960
tctgaagcaa acttcttaca gtgaaaattc attataaggg tttagacctc cttatggaga 10020
cgttcaatct gtaaactcaa gagaaggcta caagtgcctc ctttaaactg ttttcatctc 10080
acaaggatgt tagtagaaag taaacagaag agtcatatct gttttcacag cccaattata 10140
cagaaatccg acagtactgc aatcactggc gaaattttgc tgacattgat gattcctgga 10200
aaagtataaa gagtatcttg gactggacat cttttaacca ggagagaatt gttgatgttg 10260
ctggaccagg gggttggaat gacccagata tggtaaaaac ttgagccctc cttgttcaag 10320
accctgcggt aggcttgttt cctattttga cattcaaggt aaatacaggt aaagttcctg 10380
ggaggaggct ttatgtgaga gtacttagag caggatgctg tggaaagtgg tttctccata 10440
tgggtcatct aggtaacttt aagaatgttt cctcctctct tgtttgaatt atttcattct 10500
ttttctcagt tagtgattgg caactttggc ctcagctgga atcagcaagt aactcagatg 10560
gccctctggg ctatcatggc tgctccttta ttcatgtcta atgacctccg acacatcagc 10620
cctcaagcca aagctctcct tcaggataag gacgtaattg ccatcaatca ggaccccttg 10680
ggcaagcaag ggtaccagct tagacaggta aataagagta tatattttaa gatggcttta 10740
tatacccaat accaactttg tcttgggcct aaatctattt ttttcccttg ctcttgatgt 10800
tactatcagt aataaagctt cttgctagaa acattacttt atttccaaaa taatgctaca 10860
ggatcatttt aatttttcct acaagtgctt gatagttctg acattaagaa tgaatgccaa 10920
actaacaggg ccacttatca ctagttgcta agcaaccaca ctttcttggt ttttcaggga 10980
gacaactttg aagtgtggga acgacctctc tcaggcttag cctgggctgt agctatgata 11040
aaccggcagg agattggtgg acctcgctct tataccatcg cagttgcttc cctgggtaaa 11100
ggagtggcct gtaatcctgc ctgcttcatc acacagctcc tccctgtgaa aaggaagcta 11160
gggttctatg aatggacttc aaggttaaga agtcacataa atcccacagg cactgttttg 11220
cttcagctag aaaatacaat gcagatgtca ttaaaagact tactttaaaa tgtttatttt 11280
attgccaact actacttcct gtccaccttt ttctccattc actttaaaag ctcaaggcta 11340
ggtggctcat gcctgtaatc ccagcacttt gggaggctga ggcgggcaga tcacctgagg 11400
tcgggacttt gagacccgcc tggacaacat ggtgaaaccc catttctaat aaaaatataa 11460
aaattagcca ggtgtggtgg cgcacctgtg gtcccagcta ctctgggggc tgaggcatga 11520
gaatcgcttg aacccgggag tggaggttgc attgagctga gatcatgcca cctcactcca 11580
gcctgggcaa caaagattcc atctcaaaaa aaaaaaaaaa gccaggcaca gtggctcatg 11640
cctggaatcc cagcactttt ggaagctgag gcaggcagat cacttgaggt taggatttca 11700
agaccagcct ggctaacata gtaaagccct gtctctacta aaaatacaaa aattagccag 11760
gtatggtggc gagcttctgt agccccagct actcaggaga ctgaggcagg agaatcactt 11820

-continued gaacccggga agtggggggg tgcagtgacc caagatcacg ccactgcatt ccagcctggg 11880
caacagagca agactccatc tcaaaaaaaa aagttctatt tccttgaata aaattttccg 11940
aagtttaaac tttaggaata aaactattaa acccgtattt actcatccag atacccaccc 12000
cccttgttga gattctctcc caattatcaa aatgtgtagc atatttaact accaagagct 12060
aaacatcatt aagactgaaa tgtattaaga aggatgtata ggccaggcac ggtgtctcac 12120
gcctgtaatc ccaacacttt gggaggccaa gtcgggcgga tcacgaggtc aggagatgga 12180
gaccatcctg gccaacatgg tgaaaccccc tctctactaa aaatacaaaa attagccagg 12240
caggtggcag gcacctgtaa tcccagctac tccagaggct gaggcaggac aatcacttga 12300
acctgggagg cagaggctgc agtgagctga ggttgtacca attgcactcc agcctaggta 12360
acgagcaaca ctccatctca aaaaaagaaa aaaaaaaaga tgtataattt ggaactgtta 12420
agaggcattt taaaga 12436

<210> SEQ ID NO 2
<211> LENGTH: 429
<212> TYPE: PRT
<213> ORGANISM: Homo sapiens

<400> SEQUENCE: 2

Met Gln Leu Arg Asn Pro Glu Leu His Leu Gly Cys Ala Leu Ala Leu
1 5 10 15

Arg Phe Leu Ala Leu Val Ser Trp Asp Ile Pro Gly Ala Arg Ala Leu
20 25 30

Asp Asn Gly Leu Ala Arg Thr Pro Thr Met Gly Trp Leu His Trp Glu
35 40 45

Arg Phe Met Cys Asn Leu Asp Cys Gln Glu Glu Pro Asp Ser Cys Ile
50 55 60

Ser Glu Lys Leu Phe Met Glu Met Ala Glu Leu Met Val Ser Glu Gly
65 70 75 80

Trp Lys Asp Ala Gly Tyr Glu Tyr Leu Cys Ile Asp Asp Cys Trp Met
85 90 95

Ala Pro Gln Arg Asp Ser Glu Gly Arg Leu Gln Ala Asp Pro Gln Arg
100 105 110

Phe Pro His Gly Ile Arg Gln Leu Ala Asn Tyr Val His Ser Lys Gly
115 120 125

Leu Lys Leu Gly Ile Tyr Ala Asp Val Gly Asn Lys Thr Cys Ala Gly
130 135 140

Phe Pro Gly Ser Phe Gly Tyr Tyr Asp Ile Asp Ala Gln Thr Phe Ala
145 150 155 160

Asp Trp Gly Val Asp Leu Leu Lys Phe Asp Gly Cys Tyr Cys Asp Ser
165 170 175

Leu Glu Asn Leu Ala Asp Gly Tyr Lys His Met Ser Leu Ala Leu Asn
180 185 190

Arg Thr Gly Arg Ser Ile Val Tyr Ser Cys Glu Trp Pro Leu Tyr Met
195 200 205

Trp Pro Phe Gln Lys Pro Asn Tyr Thr Glu Ile Arg Gln Tyr Cys Asn
210 215 220

His Trp Arg Asn Phe Ala Asp Ile Asp Asp Ser Trp Lys Ser Ile Lys
225 230 235 240

Ser Ile Leu Asp Trp Thr Ser Phe Asn Gln Glu Arg Ile Val Asp Val
245 250 255

-continued

```
Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425
```

<210> SEQ ID NO 3
<211> LENGTH: 1290
<212> TYPE: DNA
<213> ORGANISM: Homo sapiens

<400> SEQUENCE: 3

```
atgcagctga ggaatcccga gctccacctg ggctgtgctc tggctctgcg gttcctggcc     60

ctcgtgtcct gggacatccc tggcgctagg gccctcgata acggactggc ccggaccccc    120

acaatgggat ggctccactg ggaaaggttc atgtgcaatc tggactgtca ggaggaaccc    180

gactcctgca tcagcgaaaa gctcttcatg gagatggccg agctgatggt gagcgagggc    240

tggaaggacg ccggctacga gtatctgtgc atcgatgact gctggatggc ccctcaaagg    300

gactccgaag gcaggctgca ggctgatccc caaaggtttc cccacggaat ccggcagctc    360

gccaactacg tgcattccaa gggcctcaag ctcggcatct acgccgacgt gggcaacaaa    420

acatgcgccg gattccccgg cagcttcggc tactacgaca tcgacgccca gacattcgct    480

gattggggag tggacctgct gaagttcgac ggctgttact gcgattccct ggaaaacctg    540

gccgacggct acaaacacat gtccctcgcc ctgaaccgga caggcaggtc catcgtgtac    600

agctgcgagt ggcccctgta catgtggcct ttccagaagc ccaactacac agagatcagg    660

cagtactgca accactggag gaacttcgct gacatcgacg actcctggaa gagcatcaag    720

agcatcctgg actggaccag cttcaaccag gagaggatcg tggacgtggc tggacccgga    780

ggctggaacg accccgatat gctggtgatt ggcaacttcg gactgagctg gaaccagcag    840

gtgacccaga tggccctgtg ggccattatg gccgctcccc tgttcatgtc caacgacctg    900

aggcacatca gcccccaggc caaggctctg ctgcaggaca aggatgtgat cgccatcaac    960

caggaccccc tgggcaagca gggctaccag ctgaggcaag gagataactt cgaggtgtgg   1020

gagaggcccc tgtccggact ggcttgggcc gtggccatga tcaatcggca ggagatcggc   1080

ggaccccggt cctacaccat tgctgtggcc agcctgggaa aaggagtcgc ctgcaacccc   1140
```

-continued

```
gcctgcttca ttacccagct gctccccgtg aagcggaagc tgggcttcta tgagtggacc   1200

agcaggctga ggtcccatat caatcctacc ggcaccgtcc tcctccagct cgagaatacc   1260

atgcagatga gcctcaagga tctgctgtga                                    1290
```

METHODS OF TREATING FABRY DISEASE IN PATIENTS HAVING A MUTATION IN THE GLA GENE

CROSS-REFERENCE TO RELATED APPLICATIONS

This application is the National Stage entry of PCT/US2019/013761, filed on Jan. 16, 2019, which claims priority to United States Provisional Application. Ser. No. 62/719,962, filed Aug. 20, 2018, the entire disclosures of which are hereby incorporated by reference herein.

TECHNICAL FIELD

Principles and embodiments of the present invention relate generally to the use of pharmacological chaperones for the treatment of Fabry disease, particularly in patients with mutations or variants in the α-galactosidase (GLA) gene.

BACKGROUND

Many human diseases result from mutations that cause changes in the amino acid sequence of a protein which reduce its stability and may prevent it from folding properly. Proteins generally fold in a specific region of the cell known as the endoplasmic reticulum, or ER. The cell has quality control mechanisms that ensure that proteins are folded into their correct three-dimensional shape before they can move from the ER to the appropriate destination in the cell, a process generally referred to as protein trafficking. Misfolded proteins are often eliminated by the quality control mechanisms after initially being retained in the ER. In certain instances, misfolded proteins can accumulate in the ER before being eliminated. The retention of misfolded proteins in the ER interrupts their proper trafficking, and the resulting reduced biological activity can lead to impaired cellular function and ultimately to disease. In addition, the accumulation of misfolded proteins in the ER may lead to various types of stress on cells, which may also contribute to cellular dysfunction and disease.

Such mutations can lead to lysosomal storage disorders (LSDs), which are characterized by deficiencies of lysosomal enzymes due to mutations in the genes encoding the lysosomal enzymes. The resultant disease causes the pathologic accumulation of substrates of those enzymes, which include lipids, carbohydrates, and polysaccharides. Although there are many different mutant genotypes associated with each LSD, many of the mutations are missense mutations which can lead to the production of a less stable enzyme. These less stable enzymes are sometimes prematurely degraded by the ER-associated degradation pathway. This results in the enzyme deficiency in the lysosome, and the pathologic accumulation of substrate. Such mutant enzymes are sometimes referred to in the pertinent art as "folding mutants" or "conformational mutants."

Fabry Disease is a LSD caused by a mutation to the GLA gene, which encodes the enzyme α-galactosidase A (α-Gal A). α-Gal A is required for glycosphingolipid metabolism. The mutation causes the substrate globotriaosylceramide (GL-3) to accumulate in various tissues and organs. Males with Fabry disease are hemizygotes because the disease genes are encoded on the X chromosome. Fabry disease is estimated to affect 1 in 40,000 and 60,000 males, and occurs less frequently in females.

There have been several approaches to treatment of Fabry disease. One approved therapy for treating Fabry disease is enzyme replacement therapy (ERT), which typically involves intravenous infusion of a purified form of the corresponding wild-type protein. Two α-Gal A products are currently available for the treatment of Fabry disease: agalsidase alfa (Replagal®, Shire Human Genetic Therapies) and agalsidase beta (Fabrazyme®; Sanofi Genzyme Corporation). ERT has several drawbacks, however. One of the main complications with ERT is rapid degradation of the infused protein, which leads to the need for numerous costly high dose infusions. ERT has several additional caveats, such as difficulties with large-scale generation, purification, and storage of properly folded protein; obtaining glycosylated native protein; generation of an anti-protein immune response; and inability of protein to cross the blood-brain barrier to mitigate central nervous system pathologies (i.e., low bioavailability). In addition, replacement enzyme cannot penetrate the heart or kidney in sufficient amounts to reduce substrate accumulation in the renal podocytes or cardiac myocytes, which figure prominently in Fabry pathology.

Another approach to treating some enzyme deficiencies involves the use of small molecule inhibitors to reduce production of the natural substrate of deficient enzyme proteins, thereby ameliorating the pathology. This "substrate reduction" approach has been specifically described for a class of about 40 LSDs that include glycosphingolipid storage disorders. The small molecule inhibitors proposed for use as therapy are specific for inhibiting the enzymes involved in synthesis of glycolipids, reducing the amount of cellular glycolipid that needs to be broken down by the deficient enzyme.

A third approach to treating Fabry disease has been treatment with what are called pharmacological chaperones (PCs). Such PCs include small molecule inhibitors of α-Gal A, which can bind to the α-Gal A to increase the stability of both mutant enzyme and the corresponding wild type. However, patients for PC therapy should have an amenable mutation or variant which results in the production of an enzyme that has the potential to be stabilized and folded into a conformation that permits trafficking out of the ER.

Thus, even when Fabry disease is diagnosed by detecting deficient α-Gal A activity in plasma or peripheral leukocytes (WBCs), it is very difficult, if not impossible, to predict whether a particular Fabry patient will respond to treatment with a PC. Thus, there remains a need to identify new GLA mutations or variants that will be responsive to a PC and make available new methods of treatment to Fabry patients with these mutations or variants.

SUMMARY

One aspect of the invention pertains to a method of treating a patient diagnosed with Fabry disease. The method comprises administering to the patient a therapeutically effective dose of a pharmacological chaperone for α-Gal A, wherein the patient has a missense mutation of the nucleic acid sequence encoding α-Gal A. In one or more embodiments, the mutation is D33H, G35A, Y88S, T194A, W204G, Y216S, Q250K, or R392T. In one or more embodiments, the mutation is N53K, Q57R, S62delinsLA, M96V, R112L, D155E, N228D, Q330P, V339A, K391E, or N408Y. In one or more embodiments, the mutation is V22G, N34H, G80V, Q107R, Y152D, A156S, L189F, W204L, S238G, 1239M, A257V, P259Q, N320H, P323T, E338V, P380L, or T412P. In various embodiments, these mutations are relative to SEQ ID NO: 2. In one or more embodiments, the mutation is D33H relative to SEQ ID NO: 2. In one or more embodiments, the mutation is G35A relative to SEQ ID NO: 2. In one or more embodiments, the mutation is Y88S relative to SEQ ID NO: 2. In one or more embodiments, the mutation is T194A relative to SEQ ID NO: 2. In one or more embodiments, the mutation is W204G relative to SEQ ID NO: 2. In one or more embodiments, the mutation is Y216S relative to SEQ ID NO: 2. In one or more embodiments, the mutation is Q250K relative to SEQ ID NO: 2. In one or more embodiments, the mutation is R392T relative to SEQ ID NO: 2. In one or more embodiments, the mutation is N53K relative to SEQ ID NO: 2. In one or more embodiments, the mutation is Q57R relative to SEQ ID NO: 2. In one or more embodiments, the mutation is S62delinsLA relative to SEQ ID NO: 2. In one or more embodiments, the mutation is M96V relative to SEQ ID NO: 2. In one or more embodiments, the mutation is R112L relative to SEQ ID NO: 2. In one or more embodiments, the mutation is D155E relative to SEQ ID NO: 2. In one or more embodiments, the mutation is N228D relative to SEQ ID NO: 2. In one or more embodiments, the mutation is Q330P relative to SEQ ID NO: 2. In one or more embodiments, the mutation is V339A relative to SEQ ID NO: 2. In one or more embodiments, the mutation is K391E relative to SEQ ID NO: 2. In one or more embodiments, the mutation is N408Y relative to SEQ ID NO: 2. In one or more embodiments, the mutation is V22G relative to SEQ ID NO: 2. In one or more embodiments, the mutation is N34H relative to SEQ ID NO: 2. In one or more embodiments, the mutation is G80V relative to SEQ ID NO: 2. In one or more embodiments, the mutation is Q107R relative to SEQ ID NO: 2. In one or more embodiments, the mutation is Y152D relative to SEQ ID NO: 2. In one or more embodiments, the mutation is A156S relative to SEQ ID NO: 2. In one or more embodiments, the mutation is L189F relative to SEQ ID NO: 2. In one or more embodiments, the mutation is W204L relative to SEQ ID NO: 2. In one or more embodiments, the mutation is S238G relative to SEQ ID NO: 2. In one or more embodiments, the mutation is 1239M relative to SEQ ID NO: 2. In one or more embodiments, the mutation is A257V relative to SEQ ID NO: 2. In one or more embodiments, the mutation is P259Q relative to SEQ ID NO: 2. In one or more embodiments, the mutation is N320H relative to SEQ ID NO: 2. In one or more embodiments, the mutation is P323T relative to SEQ ID NO: 2. In one or more embodiments, the mutation is E338V relative to SEQ ID NO: 2. In one or more embodiments, the mutation is P380L relative to SEQ ID NO: 2. In one or more embodiments, the mutation is T412P relative to SEQ ID NO: 2. In some embodiments, the pharmacological chaperone comprises migalastat or salt thereof. In one or more embodiments, the dose of migalastat or salt thereof is from about 100 mg to about 150 mg free base equivalent (FBE). In some embodiments, the salt of migalastat is migalastat hydrochloride. In one or more embodiments, the dose is about 150 mg every other day of migalastat hydrochloride or an equivalent dose of migalastat or a salt thereof other than the hydrochloride salt. In some embodiments, the migalastat or salt thereof is administered orally or by injection. These embodiments may be combined with one another or with other embodiments of the invention, for example embodiments relating to a method of enhancing α-Gal A in a patient diagnosed with or suspected of having Fabry disease, use of a pharmacological chaperone for α-Gal A for the manufacture of a medicament for treating a patient diagnosed with Fabry disease or to a pharmacological chaperone for α-Gal A for use in treating a patient diagnosed with Fabry disease as well as embodiments relating to amenable mutations, suitable PCs and dosages, formulations and routes of administration thereof.

Another aspect of the invention pertains to a method of enhancing α-Gal A in a patient diagnosed with or suspected of having Fabry disease. The method comprises administering to a patient a therapeutically effective dose of a pharmacological chaperone for α-Gal A, wherein the patient has a missense mutation in the nucleic acid sequence encoding α-Gal A. In one or more embodiments, the mutation is D33H, G35A, Y88S, T194A, W204G, Y216S, Q250K, or R392T. In one or more embodiments, the mutation is N53K, Q57R, S62delinsLA, M96V, R112L, D155E, N228D, Q330P, V339A, K391E, or N408Y. In one or more embodiments, the mutation is V22G, N34H, G80V, Q107R, Y152D, A156S, L189F, W204L, S238G, 1239M, A257V, P259Q, N320H, P323T, E338V, P380L, or T412P. In various embodiments, these mutations are relative to SEQ ID NO: 2. In one or more embodiments, the mutation is D33H relative to SEQ ID NO: 2. In one or more embodiments, the mutation is G35A relative to SEQ ID NO: 2. In one or more embodiments, the mutation is Y88S relative to SEQ ID NO: 2. In one or more embodiments, the mutation is T194A relative to SEQ ID NO: 2. In one or more embodiments, the mutation is W204G relative to SEQ ID NO: 2. In one or more embodiments, the mutation is Y216S relative to SEQ ID NO: 2. In one or more embodiments, the mutation is Q250K relative to SEQ ID NO: 2. In one or more embodiments, the mutation is R392T relative to SEQ ID NO: 2. In one or more embodiments, the mutation is N53K relative to SEQ ID NO: 2. In one or more embodiments, the mutation is Q57R relative to SEQ ID NO: 2. In one or more embodiments, the mutation is S62delinsLA relative to SEQ ID NO: 2. In one or more embodiments, the mutation is M96V relative to SEQ ID NO: 2. In one or more embodiments, the mutation is R112L relative to SEQ ID NO: 2. In one or more embodiments, the mutation is D155E relative to SEQ ID NO: 2. In one or more embodiments, the mutation is N228D relative to SEQ ID NO: 2. In one or more embodiments, the mutation is Q330P relative to SEQ ID NO: 2. In one or more embodiments, the mutation is V339A relative to SEQ ID NO: 2. In one or more embodiments, the mutation is K391E relative to SEQ ID NO: 2. In one or more embodiments, the mutation is N408Y relative to SEQ ID NO: 2. In one or more embodiments, the mutation is V22G relative to SEQ ID NO: 2. In one or more embodiments, the mutation is N34H relative to SEQ ID NO: 2. In one or more embodiments, the mutation is G80V relative to SEQ ID NO: 2. In one or more embodiments, the mutation is Q107R relative to SEQ ID NO: 2. In one or more embodiments, the mutation is Y152D relative to SEQ ID NO: 2. In one or more embodiments, the mutation is A156S relative to SEQ ID NO: 2. In one or more embodiments, the mutation is L189F relative to SEQ ID NO: 2. In one or more embodiments, the mutation is W204L relative to SEQ ID NO: 2. In one or more embodiments, the mutation is S238G relative to SEQ ID NO: 2. In one or more embodiments, the mutation is 1239M relative to SEQ ID NO: 2. In one or more embodiments, the mutation is A257V relative to SEQ ID NO: 2. In one or more embodiments, the mutation is P259Q relative to SEQ ID NO: 2. In one or more embodiments, the mutation is N320H relative to SEQ ID NO: 2. In one or more embodiments, the mutation is P323T relative to SEQ ID NO: 2. In one or more embodiments, the mutation is E338V relative to SEQ ID NO: 2. In one or more embodiments, the mutation is P380L relative to SEQ ID NO: 2. In one or more embodiments, the mutation is T412P relative to SEQ ID NO: 2. In some embodiments, the pharmacological chaperone comprises migalastat or salt thereof. In one or more embodiments, the dose of migalastat or salt thereof is from about 100 mg to about 150 mg FBE. In some embodiments, the salt of migalastat is migalastat hydrochloride. In one or more embodiments, the dose is about 150 mg every other day of migalastat hydrochloride or an equivalent dose of migalastat or a salt thereof other than the hydrochloride salt. In some embodiments, the migalastat or salt thereof is administered orally or by injection. These embodiments may be combined with one another or with other embodiments of the invention, for example embodiments relating to a method of treating a patient with Fabry disease, use of a pharmacological chaperone for α-Gal A for the manufacture of a medicament for treating a patient diagnosed with Fabry disease or to a pharmacological chaperone for α-Gal A for use in treating a patient diagnosed with Fabry disease as well as embodiments relating to amenable mutations, suitable PCs and dosages, formulations and routes of administration thereof.

Another aspect of the invention pertains to use of a pharmacological chaperone for α-Gal A for the manufacture of a medicament for treating a patient diagnosed with Fabry disease, wherein the patient has a missense mutation in the nucleic acid sequence encoding α-Gal A. In one or more embodiments, the mutation is D33H, G35A, Y88S, T194A, W204G, Y216S, Q250K, or R392T. In one or more embodiments, the mutation is N53K, Q57R, S62delinsLA, M96V, R112L, D155E, N228D, Q330P, V339A, K391E, or N408Y. In one or more embodiments, the mutation is V22G, N34H, G80V, Q107R, Y152D, A156S, L189F, W204L, S238G, 1239M, A257V, P259Q, N320H, P323T, E338V, P380L, or T412P. In various embodiments, these mutations are relative to SEQ ID NO: 2. In one or more embodiments, the mutation is D33H relative to SEQ ID NO: 2. In one or more embodiments, the mutation is G35A relative to SEQ ID NO: 2. In one or more embodiments, the mutation is Y88S relative to SEQ ID NO: 2. In one or more embodiments, the mutation is T194A relative to SEQ ID NO: 2. In one or more embodiments, the mutation is W204G relative to SEQ ID NO: 2. In one or more embodiments, the mutation is Y216S relative to SEQ ID NO: 2. In one or more embodiments, the mutation is Q250K relative to SEQ ID NO: 2. In one or more embodiments, the mutation is R392T relative to SEQ ID NO: 2. In one or more embodiments, the mutation is N53K relative to SEQ ID NO: 2. In one or more embodiments, the mutation is Q57R relative to SEQ ID NO: 2. In one or more embodiments, the mutation is S62delinsLA relative to SEQ ID NO: 2. In one or more embodiments, the mutation is M96V relative to SEQ ID NO: 2. In one or more embodiments, the mutation is R112L relative to SEQ ID NO: 2. In one or more embodiments, the mutation is D155E relative to SEQ ID NO: 2. In one or more embodiments, the mutation is N228D relative to SEQ ID NO: 2. In one or more embodiments, the mutation is Q330P relative to SEQ ID NO: 2. In one or more embodiments, the mutation is V339A relative to SEQ ID NO: 2. In one or more embodiments, the mutation is K391E relative to SEQ ID NO: 2. In one or more embodiments, the mutation is N408Y relative to SEQ ID NO: 2. In one or more embodiments, the mutation is V22G relative to SEQ ID NO: 2. In one or more embodiments, the mutation is N34H relative to SEQ ID NO: 2. In one or more embodiments, the mutation is G80V relative to SEQ ID NO: 2. In one or more embodiments, the mutation is Q107R relative to SEQ ID NO: 2. In one or more embodiments, the mutation is Y152D relative to SEQ ID NO: 2. In one or more embodiments, the mutation is A156S relative to SEQ ID NO: 2. In one or more embodiments, the mutation is L189F relative to SEQ ID NO: 2. In one or more embodiments, the mutation is W204L relative to SEQ ID NO: 2. In one or more embodiments, the mutation is S238G relative to SEQ ID NO: 2. In one or more embodiments, the mutation is 1239M relative to SEQ ID NO: 2. In one or more embodiments, the mutation is A257V relative to SEQ ID NO: 2. In one or more embodiments, the mutation is P259Q relative to SEQ ID NO: 2. In one or more embodiments, the mutation is N320H relative to SEQ ID NO: 2. In one or more embodiments, the mutation is P323T relative to SEQ ID NO: 2. In one or more embodiments, the mutation is E338V relative to SEQ ID NO: 2. In one or more embodiments, the mutation is P380L relative to SEQ ID NO: 2. In one or more embodiments, the mutation is T412P relative to SEQ ID NO: 2. In some embodiments, the pharmacological chaperone comprises migalastat or salt thereof. In one or more embodiments, the dose of migalastat or salt thereof is from about 100 mg to about 150 mg FBE. In some embodiments, the salt of migalastat is migalastat hydrochloride. In one or more embodiments, the dose is about 150 mg every other day of migalastat hydrochloride or an equivalent dose of migalastat or a salt thereof other than the hydrochloride salt. In some embodiments, the migalastat or salt thereof is administered orally or by injection. These embodiments may be combined with one another or with other embodiments of the invention, for example embodiments relating to a method of treating a patient with Fabry disease, a method of enhancing α-Gal A in a patient diagnosed with or suspected of having Fabry disease, or to a pharmacological chaperone for α-Gal A for use in treating a patient diagnosed with Fabry disease as well as embodiments relating to amenable mutations, suitable PCs and dosages, formulations and routes of administration thereof.

Another aspect of the invention pertains to a pharmacological chaperone for α-Gal A for use in treating a patient diagnosed with Fabry disease, wherein the patient has a missense mutation in the nucleic acid sequence encoding α-Gal A. In one or more embodiments, the mutation is D33H, G35A, Y88S, T194A, W204G, Y216S, Q250K, or R392T. In one or more embodiments, the mutation is N53K, Q57R, S62delinsLA, M96V, R112L, D155E, N228D, Q330P, V339A, K391E, or N408Y. In one or more embodiments, the mutation is V22G, N34H, G80V, Q107R, Y152D, A156S, L189F, W204L, S238G, 1239M, A257V, P259Q, N320H, P323T, E338V, P380L, or T412P. In various embodiments, these mutations are relative to SEQ ID NO: 2. In one or more embodiments, the mutation is D33H relative to SEQ ID NO: 2. In one or more embodiments, the mutation is G35A relative to SEQ ID NO: 2. In one or more embodiments, the mutation is Y88S relative to SEQ ID NO: 2. In one or more embodiments, the mutation is T194A relative to SEQ ID NO: 2. In one or more embodiments, the mutation is W204G relative to SEQ ID NO: 2. In one or more embodiments, the mutation is Y216S relative to SEQ ID NO: 2. In one or more embodiments, the mutation is Q250K relative to SEQ ID NO: 2. In one or more embodiments, the mutation is R392T relative to SEQ ID NO: 2. In one or more embodiments, the mutation is N53K relative to SEQ ID NO: 2. In one or more embodiments, the mutation is Q57R relative to SEQ ID NO: 2. In one or more embodiments, the mutation is S62delinsLA relative to SEQ ID NO: 2. In one or more embodiments, the mutation is M96V relative to SEQ ID NO: 2. In one or more embodiments, the mutation is R112L relative to SEQ ID NO: 2. In one or more embodiments, the mutation is D155E relative to SEQ ID NO: 2. In one or more embodiments, the mutation is N228D relative to SEQ ID NO: 2. In one or more embodiments, the mutation is Q330P relative to SEQ ID NO: 2. In one or more embodiments, the mutation is V339A relative to SEQ ID NO: 2. In one or more embodiments, the mutation is K391E relative to SEQ ID NO: 2. In one or more embodiments, the mutation is N408Y relative to SEQ ID NO: 2. In one or more embodiments, the mutation is V22G relative to SEQ ID NO: 2. In one or more embodiments, the mutation is N34H relative to SEQ ID NO: 2. In one or more embodiments, the mutation is G80V relative to SEQ ID NO: 2. In one or more embodiments, the mutation is Q107R relative to SEQ ID NO: 2. In one or more embodiments, the mutation is Y152D relative to SEQ ID NO: 2. In one or more embodiments, the mutation is A156S relative to SEQ ID NO: 2. In one or more embodiments, the mutation is L189F relative to SEQ ID NO: 2. In one or more embodiments, the mutation is W204L relative to SEQ ID NO: 2. In one or more embodiments, the mutation is S238G relative to SEQ ID NO: 2. In one or more embodiments, the mutation is I239M relative to SEQ ID NO: 2. In one or more embodiments, the mutation is A257V relative to SEQ ID NO: 2. In one or more embodiments, the mutation is P259Q relative to SEQ ID NO: 2. In one or more embodiments, the mutation is N320H relative to SEQ ID NO: 2. In one or more embodiments, the mutation is P323T relative to SEQ ID NO: 2. In one or more embodiments, the mutation is E338V relative to SEQ ID NO: 2. In one or more embodiments, the mutation is P380L relative to SEQ ID NO: 2. In one or more embodiments, the mutation is T412P relative to SEQ ID NO: 2. In some embodiments, the pharmacological chaperone comprises migalastat or salt thereof. In one or more embodiments, the dose of migalastat or salt thereof is from about 100 mg to about 150 mg FBE. In some embodiments, the salt of migalastat is migalastat hydrochloride. In one or more embodiments, the dose is about 150 mg every other day of migalastat hydrochloride or an equivalent dose of migalastat or a salt thereof other than the hydrochloride salt. In some embodiments, the migalastat or salt thereof is administered orally or by injection. These embodiments may be combined with one another or with other embodiments of the invention, for example embodiments relating to a method of treating a patient with Fabry disease, a method of enhancing α-Gal A in a patient diagnosed with or suspected of having Fabry disease or use of a pharmacological chaperone for α-Gal A for the manufacture of a medicament for treating a patient diagnosed with Fabry disease as well as embodiments relating to amenable mutations, suitable PCs and dosages, formulations and routs of administration thereof.

Various embodiments are listed below. It will be understood that the embodiments listed below may be combined not only as listed below, but in other suitable combinations in accordance with the scope of the invention.

BRIEF DESCRIPTION OF THE DRAWINGS

FIGS. 1A-E shows the full DNA sequence of human wild type GLA gene (SEQ ID NO: 1);

FIG. 2 shows the wild-type α-Gal A protein (SEQ ID NO: 2); and

FIG. 3 shows the nucleic acid sequence encoding the wild-type α-Gal A protein (SEQ ID NO: 3).

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Various aspects of the invention pertain to identification of new GLA mutations in Fabry patients who will respond to treatment with pharmacological chaperones. Other aspects of the invention pertain to the treatment of these Fabry patients, as well. For example, it has been unexpectedly discovered that the low α-Gal A activity resulting from the missense mutations D33H, G35A, Y88S, T194A, W204G, Y216S, Q250K, R392T, N53K, Q57R, S62delinsLA, M96V, R112L, D155E, N228D, Q330P, V339A, K391E, N408Y, V22G, N34H, G80V, Q107R, Y152D, A156S, L189F, W204L, S238G, I239M, A257V, P259Q, N320H, P323T, E338V, P380L, or T412P in α-Gal A can be increased when exposed to pharmacological chaperones. By extension, patients with these mutations will be responsive to treatment with pharmacological chaperones.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "Fabry disease" refers to an X-linked inborn error of glycosphingolipid catabolismdue to deficient lysosomal α-Gal A activity. This defect causes accumulation of the substrate globotriaosylceramide (("GL-3", also known as $Gb_3$ or ceramide trihexoside) and related glycosphingolipids in vascular endothelial lysosomes of the heart, kidneys, skin, and other tissues. Another substrate of the enzyme is plasma globotriaosylsphingosine ("plasma lyso-$Gb_3$").

A "carrier" is a female who has one X chromosome with a defective α-Gal A gene and one X chromosome with the normal gene and in whom X chromosome inactivation of the normal allele is present in one or more cell types. A carrier is often diagnosed with Fabry disease.

A "patient" refers to a subject who has been diagnosed with or is suspected of having a particular disease. The patient may be human or animal.

A "Fabry patient" refers to an individual who has been diagnosed with or suspected of having Fabry disease and has a mutated α-Gal A as defined further below. Characteristic markers of Fabry disease can occur in male hemizygotes and female carriers with the same prevalence, although females typically are less severely affected.

Human α-galactosidase A (α-Gal A) refers to an enzyme encoded by the human GLA gene. The full DNA sequence of α-Gal A, including introns and exons, is available in GenBank Accession No. X14448.1 and shown in FIGS. 1A-E (SEQ ID NO: 1). The human α-Gal A enzyme consists of 429 amino acids and is available in GenBank Accession Nos. X14448.1 and U78027 and shown in FIG. 2 (SEQ ID NO: 2). The nucleic acid sequence that only includes the coding regions (i.e. exons) of SEQ ID NO: 1 is shown in FIG. 3 (SEQ ID NO: 3).

The term "mutant protein" includes a protein which has a mutation in the gene encoding the protein which results in the inability of the protein to achieve a stable conformation under the conditions normally present in the ER. The failure to achieve a stable conformation results in a substantial amount of the enzyme being degraded, rather than being transported to the lysosome. Such a mutation is sometimes called a "conformational mutant." Such mutations include, but are not limited to, missense mutations, and in-frame small deletions and insertions. As used herein, deletions are indicated by the abbreviation "del" and insertions are indicated by the abbreviation "ins". Thus, the nucleotide change "c. 184_185insTAG" refers to an insertion of the nucleotide sequence TAG between nucleotides 184 and 185 and the protein sequence change "S62delinsLA" refers to a deletion of the amino acid S (serine) at position 62 and an insertion of the amino acid sequence LA (leucine and alanine).

As used herein in one embodiment, the term "mutant α-Gal A" includes an α-Gal A which has a mutation in the gene encoding α-Gal A which results in the inability of the enzyme to achieve a stable conformation under the conditions normally present in the ER. The failure to achieve a stable conformation results in a substantial amount of the enzyme being degraded, rather than being transported to the lysosome.

As used herein, the term "specific pharmacological chaperone" ("SPC") or "pharmacological chaperone" ("PC") refers to any molecule including a small molecule, protein, peptide, nucleic acid, carbohydrate, etc. that specifically binds to a protein and has one or more of the following effects: (i) enhances the formation of a stable molecular conformation of the protein; (ii) induces trafficking of the protein from the ER to another cellular location, preferably a native cellular location, i.e., prevents ER-associated degradation of the protein; (iii) prevents aggregation of misfolded proteins; and/or (iv) restores or enhances at least partial wild-type function and/or activity to the protein. A compound that specifically binds to e.g., α-Gal A, means that it binds to and exerts a chaperone effect on the enzyme and not a generic group of related or unrelated enzymes. More specifically, this term does not refer to endogenous chaperones, such as BiP, or to non-specific agents which have demonstrated non-specific chaperone activity against various proteins, such as glycerol, DMSO or deuterated water, i.e., chemical chaperones. In one or more embodiments of the present invention, the PC may be a reversible competitive inhibitor. In one embodiment, the PC is migalastat or a salt thereof. In another embodiment, the PC is migalastat free base (e.g., 123 mg of migalastat free base). In yet another embodiment, the PC is a salt of migalastat (e.g., 150 mg of migalastat HCl).

A "competitive inhibitor" of an enzyme can refer to a compound which structurally resembles the chemical structure and molecular geometry of the enzyme substrate to bind the enzyme in approximately the same location as the substrate. Thus, the inhibitor competes for the same active site as the substrate molecule, thus increasing the Km. Competitive inhibition is usually reversible if sufficient substrate molecules are available to displace the inhibitor, i.e., competitive inhibitors can bind reversibly. Therefore, the amount of enzyme inhibition depends upon the inhibitor concentration, substrate concentration, and the relative affinities of the inhibitor and substrate for the active site.

As used herein, the term "specifically binds" refers to the interaction of a pharmacological chaperone with a protein such as α-Gal A, specifically, an interaction with amino acid residues of the protein that directly participate in contacting the pharmacological chaperone. A pharmacological chaperone specifically binds a target protein, e.g., α-Gal A, to exert a chaperone effect on the protein and not a generic group of related or unrelated proteins. The amino acid residues of a protein that interact with any given pharmacological chaperone may or may not be within the protein's "active site." Specific binding can be evaluated through routine binding assays or through structural studies, e.g., co-crystallization, NMR, and the like. The active site for α-Gal A is the substrate binding site.

"Deficient α-Gal A activity" refers to α-Gal A activity in cells from a patient which is below the normal range as compared (using the same methods) to the activity in normal individuals not having or suspected of having Fabry or any other disease (especially a blood disease).

As used herein, the terms "enhance α-Gal A activity" or "increase α-Gal A activity" refer to increasing the amount of α-Gal A that adopts a stable conformation in a cell contacted with a pharmacological chaperone specific for the α-Gal A, relative to the amount in a cell (preferably of the same cell-type or the same cell, e.g., at an earlier time) not contacted with the pharmacological chaperone specific for the α-Gal A. This term also refers to increasing the trafficking of α-Gal A to the lysosome in a cell contacted with a pharmacological chaperone specific for the α-Gal A, relative to the trafficking of α-Gal A not contacted with the pharmacological chaperone specific for the protein. These terms refer to both wild-type and mutant α-Gal A. In one embodiment, the increase in the amount of α-Gal A in the cell is measured by measuring the hydrolysis of an artificial substrate in lysates from cells that have been treated with the PC. An increase in hydrolysis is indicative of increased α-Gal A activity.

The term "α-Gal A activity" refers to the normal physiological function of a wild-type α-Gal A in a cell. For example, α-Gal A activity includes hydrolysis of GL-3.

A "responder" is an individual diagnosed with or suspected of having a lysosomal storage disorder, such, for example Fabry disease, whose cells exhibit sufficiently increased α-Gal A activity, respectively, and/or amelioration of symptoms or enhancement in surrogate markers, in response to contact with a PC. Non-limiting examples of enhancements in surrogate markers for Fabry are lyso-$GB_3$ and those disclosed in US Patent Application Publication No. US 2010-0113517, which is hereby incorporated by reference in its entirety.

Non-limiting examples of improvements in surrogate markers for Fabry disease disclosed in US 2010/0113517 include increases in α-Gal A levels or activity in cells (e.g., fibroblasts) and tissue; reductions in of GL-3 accumulation; decreased plasma concentrations of homocysteine and vascular cell adhesion molecule-1 (VCAM-1); decreased GL-3 accumulation within myocardial cells and valvular fibrocytes; reduction in plasma lyso-$Gb_3$; reduction in cardiac hypertrophy (especially of the left ventricle), amelioration of valvular insufficiency, and arrhythmias; amelioration of proteinuria; decreased urinary concentrations of lipids such as CTH, lactosylceramide, ceramide, and increased urinary concentrations of glucosylceramide and sphingomyelin; the absence of laminated inclusion bodies (Zebra bodies) in glomerular epithelial cells; improvements in renal function; mitigation of hypohidrosis; the absence of angiokeratomas; and improvements in hearing abnormalities such as high frequency sensorineural hearing loss progressive hearing loss, sudden deafness, or tinnitus. Improvements in neurological symptoms include prevention of transient ischemic attack (TIA) or stroke; and amelioration of neuropathic pain manifesting itself as acroparaesthesia (burning or tingling in extremities). Another type of clinical marker that can be assessed for Fabry disease is the prevalence of deleterious cardiovascular manifestations. Common cardiac-related signs and symptoms of Fabry disease include left ventricular hypertrophy, valvular disease (especially mitral valve prolapse and/or regurgitation), premature coronary artery disease, angina, myocardial infarction, conduction abnormalities, arrhythmias, congestive heart failure.

The dose that achieves one or more of the aforementioned responses is a "therapeutically effective dose."

The phrase "pharmaceutically acceptable" refers to molecular entities and compositions that are physiologically tolerable and do not typically produce untoward reactions when administered to a human. In some embodiments, as used herein, the term "pharmaceutically acceptable" means approved by a regulatory agency of the Federal or a state government or listed in the U.S. Pharmacopoeia or other generally recognized pharmacopoeia for use in animals, and more particularly in humans. The term "carrier" in reference to a pharmaceutical carrier refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an mRNA band on a gel, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acids include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

The term "enzyme replacement therapy" or "ERT" refers to the introduction of a non-native, purified enzyme into an individual having a deficiency in such enzyme. The administered protein can be obtained from natural sources or by recombinant expression (as described in greater detail below). The term also refers to the introduction of a purified enzyme in an individual otherwise requiring or benefiting from administration of a purified enzyme, e.g., suffering from enzyme insufficiency. The introduced enzyme may be a purified, recombinant enzyme produced in vitro, or protein purified from isolated tissue or fluid, such as, e.g., placenta or animal milk, or from plants.

As used herein, the term "free base equivalent" or "FBE" refers to the amount of migalastat present in the migalastat or salt thereof. In other words, the term "FBE" means either an amount of migalastat free base, or the equivalent amount of migalastat free base that is provided by a salt of migalastat. For example, due to the weight of the hydrochloride salt, 150 mg of migalastat hydrochloride only provides as much migalastat as 123 mg of the free base form of migalastat. Other salts are expected to have different conversion factors, depending on the molecular weight of the salt.

The term "migalastat" encompasses migalastat free base or a pharmaceutically acceptable salt thereof (e.g., migalastat HCl), unless specifically indicated to the contrary.

The terms "mutation" and "variant" (e.g., as in "amenable mutation or variant") refer to a change in the nucleotide sequence of a gene or a chromosome. The two terms referred herein are typically used together—e.g., as in "mutation or variant"-referring to the change in nucleotide sequence stated in the previous sentence. If only one of the two terms is recited for some reason, the missing term was intended to be included and one should understand as such. Furthermore, the terms "amenable mutation" and "amenable variant" refer to a mutation or variant that is amenable to PC therapy, e.g. a mutation that is amenable to migalastat therapy. A particular type of amenable mutation or variant is a "HEK assay amenable mutation or variant", which is a mutation or variant that is determined to be amenable to migalastat therapy according to the criteria in the in vitro HEK assay described herein.

Fabry Disease

Fabry disease is a rare, progressive and devastating X-linked lysosomal storage disorder. Mutations in the GLA gene result in a deficiency of the lysosomal enzyme, α-Gal A, which is required for glycosphingolipid metabolism. Beginning early in life, the reduction in α-Gal A activity results in an accumulation of glycosphingolipids, including GL-3 and plasma lyso-$Gb_3$, and leads to the symptoms and life-limiting sequelae of Fabry disease, including pain, gastrointestinal symptoms, renal failure, cardiomyopathy, cerebrovascular events, and early mortality. Early initiation of therapy and lifelong treatment provide an opportunity to slow disease progression and prolong life expectancy.

Fabry disease encompasses a spectrum of disease severity and age of onset, although it has traditionally been divided into 2 main phenotypes, "classic" and "late-onset". The classic phenotype has been ascribed primarily to males with undetectable to low α-Gal A activity and earlier onset of renal, cardiac and/or cerebrovascular manifestations. The late-onset phenotype has been ascribed primarily to males with higher residual α-Gal A activity and later onset of these disease manifestations. Heterozygous female carriers typically express the late-onset phenotype but depending on the pattern of X-chromosome inactivation may also display the classic phenotype.

More than 1,000 Fabry disease-causing GLA mutations have been identified. Approximately 60% are missense mutations, resulting in single amino acid substitutions in the α-Gal A enzyme. Missense GLA mutations often result in the production of abnormally folded and unstable forms of α-Gal A and the majority are associated with the classic phenotype. Normal cellular quality control mechanisms in the endoplasmic reticulum block the transit of these abnormal proteins to lysosomes and target them for premature degradation and elimination. Many missense mutant forms are targets for migalastat, an α-Gal A-specific pharmacological chaperone.

The clinical manifestations of Fabry disease span a broad spectrum of severity and roughly correlate with a patient's residual α-GAL levels. The majority of currently treated patients are referred to as classic Fabry disease patients, most of whom are males. These patients experience disease of various organs, including the kidneys, heart and brain, with disease symptoms first appearing in adolescence and typically progressing in severity until death in the fourth or fifth decade of life. A number of recent studies suggest that there are a large number of undiagnosed males and females that have a range of Fabry disease symptoms, such as impaired cardiac or renal function and strokes, that usually first appear in adulthood. Individuals with this type of Fabry disease, referred to as late-onset Fabry disease, tend to have higher residual α-GAL levels than classic Fabry disease patients. Individuals with late-onset Fabry disease typically first experience disease symptoms in adulthood, and often have disease symptoms focused on a single organ, such as enlargement of the left ventricle or progressive kidney failure. In addition, late-onset Fabry disease may also present in the form of strokes of unknown cause.

Fabry patients have progressive kidney impairment, and untreated patients exhibit end-stage renal impairment by the fifth decade of life. Deficiency in α-Gal A activity leads to accumulation of GL-3 and related glycosphingolipids in many cell types including cells in the kidney. GL-3 accumulates in podocytes, epithelial cells and the tubular cells of the distal tubule and loop of Henle. Impairment in kidney function can manifest as proteinuria and reduced glomerular filtration rate.

Because Fabry disease is rare, involves multiple organs, has a wide age range of onset, and is heterogeneous, proper diagnosis is a challenge. Awareness is low among health care professionals and misdiagnoses are frequent. Diagnosis of Fabry disease is most often confirmed on the basis of decreased α-Gal A activity in plasma or peripheral leukocytes (WBCs) once a patient is symptomatic, coupled with mutational analysis. In females, diagnosis is even more challenging since the enzymatic identification of carrier females is less reliable due to random X-chromosomal inactivation in some cells of carriers. For example, some obligate carriers (daughters of classically affected males) have α-Gal A enzyme activities ranging from normal to very low activities. Since carriers can have normal α-Gal A enzyme activity in leukocytes, only the identification of an α-Gal A mutation by genetic testing provides precise carrier identification and/or diagnosis.

Also, as described above, the age of onset, progression, and severity of Fabry disease is at least partly dependent on the rate of substrate accumulation, which correlates to the enzymatic activity in lysosomes. Thus, a complete lack of residual activity can correspond to rapid substrate accumulation, and therefore a more severe form of the disease (having early onset and rapid progression). However, even small quantities of residual activity may be enough to degrade a large amounts of substrate. This in turn would lead to milder disease with later onset and slower progression because of the slowed substrate accumulation. Considering these factors, it is thought that even modest increases in enzymatic activity can reduce the effect of a severe clinical phenotype. Data suggests that for most LSDs, just 1% to 6% of normal activity has been estimated as sufficient to delay or prevent disease onset or yield a more mild form of the disease. That is, just small increases in activity could have a significant impact on substrate levels, and hence disease severity and the rate of disease progression. Conversely, it is expected that a mutant lysosomal enzyme that shows no response in vitro would also not respond in vivo.

In one or more embodiments, mutant or variant forms of α-Gal A considered to be amenable to migalastat are defined as showing a relative increase (+10 UM migalastat) of ≥1.20-fold and an absolute increase (+10 μM migalastat) of ≥3.0% wild-type when the mutant form of α-Gal A is expressed in HEK-293 cells (referred to as the "HEK assay") according to Good Laboratory Practice (GLP)-validated in vitro assay (GLP HEK or Migalastat Amenability Assay). Such mutations or variants are also referred to herein as "HEK assay amenable" mutations or variants.

Previous screening methods have been provided that assess enzyme enhancement prior to the initiation of treatment. For example, an assay using HEK-293 cells has been utilized in clinical trials to predict whether a given mutation will be responsive to pharmacological chaperone (e.g., migalastat) treatment. In this assay, cDNA constructs are created. The corresponding α-Gal A mutant forms are transiently expressed in HEK-293 cells. Cells are then incubated±migalastat (17 nM to 1 mM) for 4 to 5 days. After, α-Gal A levels are measured in cell lysates using a synthetic fluorogenic substrate (4-MU-α-Gal) or by western blot. This has been done for known disease-causing missense or small in-frame insertion/deletion mutations. Mutations that have previously been identified as responsive to a PC (e.g. migalastat) using these methods are listed in U.S. Pat. No. 8,592,362, which is hereby incorporated by reference in its entirety.

HEK assay amenable mutations include at least those mutations listed in a pharmacological reference table (e.g., the ones recited in the U.S. or International Product labels for a migalastat product such as GALAFOLD®). As used herein, "pharmacological reference table" refers to any publicly accessible written or electronic record, included in either the product label within the packaging of a migalastat product (e.g., GALAFOLD®) or in a website accessible by health care providers, that conveys whether a particular mutation or variant is responsive to migalastat (e.g., GALAFOLD®) PC therapy, and is not necessarily limited to written records presented in tabular form. In one embodiment of the present invention, a "pharmacological reference table" thus refers to any depository of information that includes one or more amenable mutations or variants. In another embodiment, a "pharmacological reference table" refers to an updated depository of amenable mutations or variants that includes the novel mutations or variants disclosed herein (i.e., D33H, G35A, Y88S, T194A, W204G, Y216S, Q250K, R392T, N53K, Q57R, S62delinsLA, M96V, R112L, D155E, N228D, Q330P, V339A, K391E, N408Y, V22G, N34H, G80V, Q107R, Y152D, A156S, L189F, W204L, S238G, I239M, A257V, P259Q, N320H, P323T, E338V, P380L, or T412P). An exemplary pharmacological reference table for HEK assay amenable mutations can be found in the summary of product characteristics and/or prescribing information for GALAFOLD® in various countries in which GALAFOLD® is approved for use, or at a website such as galafoldamenabilitytable.com orfabrygenevariantsearch.com.

However, as only certain mutations are amenable to treatment with migalastat, there is a need to identify new mutations and determine whether such mutations are amenable to migalastat therapy. As described in the Example below, several new mutations have been identified and determined to be mutations that are amenable to migalastat therapy. These mutations include D33H, G35A, Y88S, T194A, W204G, Y216S, Q250K, R392T, N53K, Q57R, S62delinsLA, M96V, R112L, D155E, N228D, Q330P, V339A, K391E, N408Y, V22G, N34H, G80V, Q107R, Y152D, A156S, L189F, W204L, S238G, 1239M, A257V, P259Q, N320H, P323T, E338V, P380L, and T412P.

Accordingly, in one or more embodiments, migalastat is used to treat Fabry disease and/or enhance α-Gal A activity in a patient having an α-Gal A mutation selected from the group consisting of: D33H, G35A, Y88S, T194A, W204G, Y216S, Q250K, and R392T. In one or more embodiments, migalastat is used to treat Fabry disease and/or enhance α-Gal A activity in a patient having an α-Gal A mutation selected from the group consisting of: N53K, Q57R, S62delinsLA, M96V, R112L, D155E, N228D, Q330P, V339A, K391E, and N408Y. In one or more embodiments, migalastat is used to treat Fabry disease and/or enhance α-Gal A activity in a patient having an α-Gal A mutation selected from the group consisting of: V22G, N34H, G80V, Q107R, Y152D, A156S, L189F, W204L, S238G, 1239M, A257V, P259Q, N320H, P323T, E338V, P380L, and T412P. In one or more embodiments, the patient has the mutation D33H. In one or more embodiments, the patient has the mutation G35A. In one or more embodiments, the patient has the mutation Y88S. In one or more embodiments, the patient has the mutation T194A. In one or more embodiments, the patient has the mutation W204G. In one or more embodiments, the patient has the mutation Y216S. In one or more embodiments, the patient has the mutation Q250K. In one or more embodiments, the patient has the mutation and R392T. In one or more embodiments, the patient has the mutation N53K. In one or more embodiments, the patient has the mutation Q57R. In one or more embodiments, the patient has the mutation S62delinsLA. In one or more embodiments, the patient has the mutation M96V. In one or more embodiments, the patient has the mutation R112L. In one or more embodiments, the patient has the mutation D155E. In one or more embodiments, the patient has the mutation N228D. In one or more embodiments, the patient has the mutation Q330P. In one or more embodiments, the patient has the mutation V339A. In one or more embodiments, the patient has the mutation V339A. In one or more embodiments, the patient has the mutation K391E. In one or more embodiments, the patient has the mutation N408Y. In one or more embodiments, the patient has the mutation V22G. In one or more embodiments, the patient has the mutation N34H. In one or more embodiments, the patient has the mutation G80V. In one or more embodiments, the patient has the mutation Q107R. In one or more embodiments, the patient has the mutation Y152D. In one or more embodiments, the patient has the mutation A156S. In one or more embodiments, the patient has the mutation L189F. In one or more embodiments, the patient has the mutation W204L. In one or more embodiments, the patient has the mutation S238G. In one or more embodiments, the patient has the mutation 1239M. In one or more embodiments, the patient has the mutation A257V. In one or more embodiments, the patient has the mutation P259Q. In one or more embodiments, the patient has the mutation N320H. In one or more embodiments, the patient has the mutation P323T. In one or more embodiments, the patient has the mutation E338V. In one or more embodiments, the patient has the mutation P380L. In one or more embodiments, the patient has the mutation T412P. In various embodiments, these α-Gal A mutations are relative to the amino acid sequence shown in SEQ ID NO: 2.

Exemplary nucleotide changes associated with these novel mutations are shown in Table 1 below:

TABLE 1

| Novel Migalastat-Amenable Mutations | | |
|---|---|---|
| Nucleotide change | Nucleotide change | Protein sequence change |
| c.97G>C | c.G97C | D33H |
| c.104G>C | c.G104C | G35A |
| c.263A>C | c.A263C | Y88S |
| c.580A>G | c.A580G | T194A |
| c.610T>G | c.T610G | W204G |
| c.647A>C | c.A647C | Y216S |
| c.748C>A | c.C748A | Q250K |
| c.1175G>C | c.G1175C | R392T |
| c.159C>G or c.159C>A | c.C159G or c.C159A | N53K |
| c.170A>G | c.A170G | Q57R |
| c.184_185insTAG | c.184_185insTAG | S62delinsLA |
| c.286A>G | c.A286G | M96V |
| c.335G>T | c.G335T | R112L |
| c.465T>A or c.465T>G | c.T465A or c.T465G | D155E |
| c.682A>G | c.A682G | N228D |
| c.989A>C | c.A989C | Q330P |
| c.1016T>C | c.T1016C | V339A |
| c.1171A>G | c.A1171G | K391E |
| c.1222A>T | c.A1222T | N408Y |
| c.65T>G | c.T65G | V22G |
| c.100A>C | c.A100C | N34H |
| c.239G>T | c.G239T | G80V |
| c.320A>G | c.A320G | Q107R |
| c.454T>G | c.T454G | Y152D |
| c.466G>T | c.G466T | A156S |
| c.567G>C or c.567G>T | c.G567C or c.G567T | L189F |
| c.611G>T | c.G611T | W204L |
| c.712A>G | c.A712G | S238G |
| c.717A>G | c.A717G | I239M |
| c.770C>T | c.C770T | A757V |
| c.776C>A | c.C776A | P259Q |
| c.958A>C | c.A958C | N320H |
| c.967C>A | c.C967A | P323T |
| c.1013A>T | c.A1013T | E338V |
| c.1139C>T | c.C1139T | P380L |
| c.1234A>C | c.A1234C | T412P |

Accordingly, in various embodiments, migalastat is used to treat Fabry disease and/or enhance α-Gal A activity in a patient having a GLA mutation selected from the group consisting of: c.97G>C, c.104G>C, c.263A>C, c.580A>G, c.610T>G, c.647A>C, c.748C>A and c.1175G>C. In some embodiments, migalastat is used to treat Fabry disease and/or enhance α-Gal A activity in a patient having a GLA mutation selected from the group consisting of: c.159C>G of c.159C>A, c.170A>G, c.184_185insTAG, c.286A>G, c.335G>T, c.465T>A of c.465T>G, c.682A>G, c.989A>C, c.1016T>C, c.1171A>G, and c.1222A>T. In some embodiments, migalastat is used to treat Fabry disease and/or enhance α-Gal A activity in a patient having a GLA mutation selected from the group consisting of: c.65T>G, c. 100A>C, c.239G>T, c.320A>G, c.454T>G, c.466G>T, c.567G>C or c.567G>T, c.611G>T, c.712A>G, c.717A>G, c.770C>T, c.776C>A, c.958A>C, c.967C>A, c.1013A>T, c. 1139C>T, and c.1234A>C. In one or more embodiments, the patient has the GLA mutation c.97G>C. In one or more embodiments, the patient has the GLA mutation c.104G>C. In one or more embodiments, the patient has the GLA mutation c.263A>C. In one or more embodiments, the patient has the GLA mutation c.580A>G. In one or more embodiments, the patient has the GLA mutation c.610T>G. In one or more embodiments, the patient has the GLA mutation c.647A>C.

In one or more embodiments, the patient has the GLA mutation c.748C>A. In one or more embodiments, the patient has the GLA mutation c.1175G>C. In one or more embodiments, the patient has the GLA mutation c.159C>G or c.159C>A. In one or more embodiments, the patient has the GLA mutation c. 170A>G. In one or more embodiments, the patient has the GLA mutation c.184_185insTAG. In one or more embodiments, the patient has the GLA mutation c.286A>G. In one or more embodiments, the patient has the GLA mutation c.335G>T. In one or more embodiments, the patient has the GLA mutation c.465T>A or c.465T>G. In one or more embodiments, the patient has the GLA mutation c.682A>G. In one or more embodiments, the patient has the GLA mutation c.989A>C. In one or more embodiments, the patient has the GLA mutation c.1016T>C. In one or more embodiments, the patient has the GLA mutation c.1171A>G. In one or more embodiments, the patient has the GLA mutation c.1222A>T. In one or more embodiments, the patient has the GLA mutation c.65T>G. In one or more embodiments, the patient has the GLA mutation c. 100A>C. In one or more embodiments, the patient has the GLA mutation c.239G>T. In one or more embodiments, the patient has the GLA mutation c.320A>G. In one or more embodiments, the patient has the GLA mutation c.454T>G. In one or more embodiments, the patient has the GLA mutation c.466G>T. In one or more embodiments, the patient has the GLA mutation c.567G>C or c.567G>T. In one or more embodiments, the patient has the GLA mutation c.611G>T. In one or more embodiments, the patient has the GLA mutation c.712A>G. In one or more embodiments, the patient has the GLA mutation c.717A>G. In one or more embodiments, the patient has the GLA mutation c.770C>T. In one or more embodiments, the patient has the GLA mutation c.776C>A. In one or more embodiments, the patient has the GLA mutation c.958A>C. In one or more embodiments, the patient has the GLA mutation c.967C>A. In one or more embodiments, the patient has the GLA mutation c.1013A>T. In one or more embodiments, the patient has the GLA mutation c.1139C>T. In one or more embodiments, the patient has the GLA mutation c.1234A>C. In various embodiments, these GLA mutations are relative to the nucleic sequence shown in SEQ ID NO: 3.

Furthermore, various embodiments of the present invention provide PCs for the treatment of Fabry disease in a patient having a mutation in the gene encoding α-Gal A, wherein the patient is identified as having a missense mutation in a human α-Gal A encoded by a nucleic acid sequence set forth in SEQ ID NO: 1 and/or SEQ ID NO: 3. Another aspect of the invention pertains a method of treating a patient diagnosed with Fabry disease. In one or more embodiments, the method comprises administering to a patient a therapeutically effective dose of a PC of α-Gal A. In further embodiments, the patient has a missense mutation in the nucleic acid sequence encoding α-Gal A. Another aspect of the invention pertains to a method of enhancing α-Gal A in a patient diagnosed with or suspected of having Fabry disease. In one or more embodiments, the method comprises administering to a patient a therapeutically effective dose of a PC of α-Gal A, wherein the patient has a mutant α-Gal A encoded by a nucleic acid sequence having a missense mutation relative to SEQ ID NO: 1 and/or SEQ ID NO: 3. Details and further embodiments of these uses and methods follows below. Any of the embodiments relating a method of treating a patient with Fabry disease, a method of enhancing α-Gal A in a patient diagnosed with or suspected of having Fabry disease, use of a pharmacological chaperone for α-Gal A for the manufacture of a medicament for treating a patient diagnosed with Fabry disease or to a pharmacological chaperone for α-Gal A for use in treating a patient diagnosed with Fabry disease wherein the patient is identified as having a missense mutation in a human α-Gal A encoded by a nucleic acid sequence set forth in SEQ ID NO: 1 and/or SEQ ID NO: 3 can be combined with any of the other embodiments of the invention, for example embodiments relating to the PCs and suitable dosages thereof.

In one or more embodiments, the patient may have other mutations in their GLA gene. For example, there may be mutations in the intron region which may or may not affect the resulting α-Gal A enzyme. Thus, in one or more embodiments, the patient has mutant α-Gal A encoded by a nucleic acid sequence having at least 95, 96, 97, 98, 99, 99.1, 99.2, 99.3, 99.4, 99.5, 99.6, 99.7, 99.8 or 99.9% identity to SEQ ID NO: 1. Furthermore, the patient may have one or more additional mutations in the coding region of the GLA gene. Thus, in one or more embodiments, the patient has mutant α-Gal A encoded by a nucleic acid sequence having at least 95, 96, 97, 98, 99, 99.1, 99.2, 99.3, 99.4, 99.5, 99.6, 99.7, 99.8 or 99.9% identity to SEQ ID NO: 3. Moreover, in one or more embodiments, the patient has 1, 2, 3, 4, 5, 6, 7, 8, 9, 10, 15, 20 or 30 mutations relative to SEQ ID NO: 1 or SEQ ID NO: 3. It is also noted that some nucleic acid mutations in SEQ ID NO: 1 or SEQ ID NO: 3 can result in no change in amino acid for the resulting protein, as various amino acids are encoded by multiple nucleic acid sequences. Again, any of these embodiments can be combined with any of the other embodiments of the invention, for example embodiments relating to amenable mutations, the PCs and suitable dosages thereof.

Pharmacological Chaperones

The binding of small molecule inhibitors of enzymes associated with LSDs can increase the stability of both mutant enzyme and the corresponding wild-type enzyme (see U.S. Pat. Nos. 6,274,597; 6,583,158; 6,589,964; 6,599,919; 6,916,829, and 7,141,582 all incorporated herein by reference). In particular, administration of small molecule derivatives of glucose and galactose, which are specific, selective competitive inhibitors for several target lysosomal enzymes, effectively increased the stability of the enzymes in cells in vitro and, thus, increased trafficking of the enzymes to the lysosome. Thus, by increasing the amount of enzyme in the lysosome, hydrolysis of the enzyme substrates is expected to increase. The original theory behind this strategy was as follows: since the mutant enzyme protein is unstable in the ER (Ishii et al., *Biochem. Biophys. Res. Comm.* 1996; 220:812-815), the enzyme protein is retarded in the normal transport pathway (ER→Golgi apparatus→endosomes→lysosome) and prematurely degraded. Therefore, a compound which binds to and increases the stability of a mutant enzyme, may serve as a "chaperone" for the enzyme and increase the amount that can exit the ER and move to the lysosomes. In addition, because the folding and trafficking of some wild-type proteins is incomplete, with up to 70% of some wild-type proteins being degraded in some instances prior to reaching their final cellular location, the chaperones can be used to stabilize wild-type enzymes and increase the amount of enzyme which can exit the ER and be trafficked to lysosomes.

In one or more embodiments, the pharmacological chaperone comprises migalastat or a salt thereof. The compound migalastat, also known as 1-deoxygalactonojirimycin (1-DGJ) or (2R,3S,4R,5S)-2-(hydroxymethyl) piperdine-3,4,5-triol is a compound having the following chemical formula:

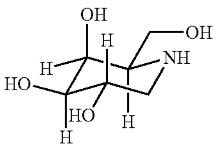 and 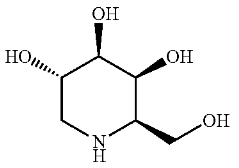

Migalastat free base

As discussed herein, pharmaceutically acceptable salts of migalastat may also be used in the present invention. When a salt of migalastat is used, the dosage of the salt will be adjusted so that the dose of migalastat received by the patient is equivalent to the amount which would have been received had the migalastat free base been used. One example of a pharmaceutically acceptable salt of migalastat is migalastat HCl:

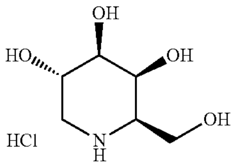

Migalastat HCl

Migalastat is a low molecular weight iminosugar and is an analogue of the terminal galactose of GL-3. In vitro and in vivo pharmacologic studies have demonstrated that migalastat acts as a pharmacological chaperone, selectively and reversibly binding, with high affinity, to the active site of wild-type α-Gal A and specific mutant forms of α-Gal A. Migalastat binding stabilizes these mutant forms of α-Gal A in the endoplasmic reticulum facilitating their proper trafficking to lysosomes where dissociation of migalastat allows α-Gal A to reduce the level of GL-3 and other substrates.

In a specific embodiment, the PC comprises migalastat or salt thereof. In further embodiments, the PC comprises migalastat hydrochloride.

Any of these PCs for α-Gal A may be used in combination with any of the other embodiments of the invention, for example embodiments relating to a method of treating a patient with Fabry disease, a method of enhancing α-Gal A in a patient diagnosed with or suspected of having Fabry disease, use of a pharmacological chaperone for α-Gal A for the manufacture of a medicament for treating a patient diagnosed with Fabry disease or to a pharmacological chaperone for α-Gal A for use in treating a patient diagnosed with Fabry disease as well as embodiments relating to suitable doses of PCs, amenable mutations and to the treatment of a Fabry patient having certain mutations in the nucleic acid sequence encoding α-Gal A.

Dosing, Formulation and Administration

In one or more embodiments, the Fabry patient is administered migalastat or salt thereof at a frequency of once every other day (also referred to as "QOD"). In various embodiments, the doses described herein pertain to migalastat hydrochloride or an equivalent dose of migalastat or a salt thereof other than the hydrochloride salt. In some embodiments, these doses pertain to the free base of migalastat. In alternate embodiments, these doses pertain to a salt of migalastat. In further embodiments, the salt of migalastat is migalastat hydrochloride. The administration of migalastat or a salt of migalastat is referred to herein as "migalastat therapy".

The effective amount of migalastat or salt thereof can be in the range from about 100 mg FBE to about 150 mg FBE. Exemplary doses include about 100 mg FBE, about 105 mg FBE, about 110 mg FBE, about 115 mg FBE, about 120 mg FBE, about 123 mg FBE, about 125 mg FBE, about 130 mg FBE, about 135 mg FBE, about 140 mg FBE, about 145 mg FBE or about 150 mg FBE.

Again, it is noted that 150 mg of migalastat hydrochloride is equivalent to 123 mg of the free base form of migalastat. Thus, in one or more embodiments, the dose is 150 mg of migalastat hydrochloride or an equivalent dose of migalastat or a salt thereof other than the hydrochloride salt, administered at a frequency of once every other day. As set forth above, this dose is referred to as 123 mg FBE of migalastat. In further embodiments, the dose is 150 mg of migalastat hydrochloride administered at a frequency of once every other day. In other embodiments, the dose is 123 mg of the migalastat free base administered at a frequency of once every other day.

In various embodiments, the effective amount is about 122 mg, about 128 mg, about 134 mg, about 140 mg, about 146 mg, about 150 mg, about 152 mg, about 159 mg, about 165 mg, about 171 mg, about 177 mg or about 183 mg of migalastat hydrochloride.

Accordingly, in various embodiments, migalastat therapy includes administering 123 mg FBE at a frequency of once every other day, such as 150 mg of migalastat hydrochloride every other day.

The administration of migalastat or salt thereof may be for a certain period of time. In one or more embodiments, the migalastat or salt thereof is administered for a duration of at least 28 days, such as at least 30, 60 or 90 days or at least 3, 4, 5, 6, 7, 8, 9, 10, 11, 12, 16, 20, 24, 30 or 36 months or at least 1, 2, 3, 4 or 5 years. In various embodiments, the migalastat therapy is long-term migalastat therapy of at least 6 months, such as at least 6, 7, 8, 9, 10, 11, 12, 16, 20, 24, 30 or 36 months or at least 1, 2, 3, 4 or 5 years.

Administration of migalastat or salt thereof according to the present invention may be in a formulation suitable for any route of administration, but is preferably administered in an oral dosage form such as a tablet, capsule or solution. As one example, the patient is orally administered capsules each containing 150 mg migalastat hydrochloride or an equivalent dose of migalastat or a salt thereof other than the hydrochloride salt.

In some embodiments, the PC (e.g., migalastat or salt thereof) is administered orally. In one or more embodiments, the PC (e.g., migalastat or salt thereof) is administered by injection. The PC may be accompanied by a pharmaceutically acceptable carrier, which may depend on the method of administration.

In one or more embodiments, the PC (e.g., migalastat or salt thereof) is administered as monotherapy, and can be in a form suitable for any route of administration, including e.g., orally in the form tablets or capsules or liquid, or in sterile aqueous solution for injection. In other embodiments, the PC is provided in a dry lyophilized powder to be added to the formulation of the replacement enzyme during or immediately after reconstitution to prevent enzyme aggregation in vitro prior to administration.

When the PC (e.g., migalastat or salt thereof) is formulated for oral administration, the tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active chaperone compound.

The pharmaceutical formulations of the PC (e.g., migalastat or salt thereof) suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate and gelatin. Sterile injectable solutions are prepared by incorporating the purified enzyme (if any) and the PC (e.g., migalastat or salt thereof) in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, bicarbonate buffer, amino acids, urea, alcohols, ascorbic acid, and phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The route of administration of the chaperone compound may be oral or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations of the chaperone compound may be by periodic injections of a bolus of the preparation, or may be administered by intravenous or intraperitoneal administration from a reservoir which is external (e.g., an i.v. bag) or internal (e.g., a bioerodable implant).

Embodiments relating to pharmaceutical formulations and administration may be combined with any of the other embodiments of the invention, for example embodiments relating to methods of treating patients with Fabry disease, use of a pharmacological chaperone for α-Gal A for the manufacture of a medicament for treating a patient diagnosed with Fabry disease or to a pharmacological chaperone for α-Gal A for use in treating a patient diagnosed with Fabry disease as well as embodiments relating to amenable mutations, the PCs and suitable dosages thereof.

In one or more embodiments, the PC (e.g., migalastat or salt thereof) is administered in combination with ERT. ERT increases the amount of protein by exogenously introducing wild-type or biologically functional enzyme by way of infusion. This therapy has been developed for many genetic disorders, including LSDs such as Fabry disease, as referenced above. After the infusion, the exogenous enzyme is expected to be taken up by tissues through non-specific or receptor-specific mechanism. In general, the uptake efficiency is not high, and the circulation time of the exogenous protein is short. In addition, the exogenous protein is unstable and subject to rapid intracellular degradation as well as having the potential for adverse immunological reactions with subsequent treatments. In one or more embodiments, the chaperone is administered at the same time as replacement enzyme (e.g., replacement α-Gal A). In some embodiments, the chaperone is co-formulated with the replacement enzyme (e.g., replacement α-Gal A).

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in various embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

Example: Effect of Migalastat on Mutations of α-Gal A

The α-Gal A activity was measured in lysates prepared from HEK-293 cells transiently transfected with the indicated mutant form of α-Gal A and incubated in the absence or presence of 10 μM migalastat for 5 days. The α-Gal A activity is expressed as the nmoles of free 4-MU released per milligram of protein per hour (nmol/mg/hr). Baseline α-Gal A activity and α-Gal A activity after incubation with 10 μM migalastat, were additionally expressed as a percentage of baseline wild-type α-Gal A activity (% WT). The wild-type α-Gal A activity that was used to calculate these percentages was the average activity measured in lysates from wild-type transfected cells, incubated in the absence of migalastat, measured in parallel.

The results of the α-Gal A activity testing for the novel mutations D33H, G35A, Y88S, T194A, W204G, Y216S, Q250K, and R392T is shown in Table 2 below:

TABLE 2

Effect of Migalastat on α-Gal A Activity

| α-Gal A Mutant Form | D33H | G35A | Y-88S | T194A | W204G | Y216S | Q250K | R392T |
|---|---|---|---|---|---|---|---|---|
| Baseline α-Gal A activity (nmol/mg/hr) | 12925 ± 915 | 19688 ± 1062 | 1510 ± 52 | 3751 ± 287 | BLD | 635 ± 64 | 4389 ± 500 | 30058 ± 1487 |
| 10 nM migalastat α-Gal A activity (nmol/mg/hr) | 24908 ± 1775 | 31694 ± 1949 | 5542 ± 376 | 10315 ± 459 | 1695 ± 198 | 11238 ± 751 | 11325 ± 1111 | 36679 ± 1896 |
| Mann-Whitney U p-value | 0.0001 | 0.0001 | 0.0001 | 0.0001 | 0.0001 | 0.0001 | 0.0001 | 0.0014 |
| Baseline α-Gal A activity (% WT) | 36.1 ± 2.4 | 51.1 ± 3.2 | 3.8 ± 0.2 | 10.8 ± 0.7 | N/A | 2.0 ± 0.2 | 16.1 ± 1.5 | 104.6 ± 6.8 |
| 10 μM migalastat α-Gal A activity(% WT) | 68.8 ± 4.3 | 82.1 ±5.6 | 14.1 ± 1.3 | 30.5 ± 2.0 | 6.5 ± 0.7 | 34.7 ± 1.8 | 41.6 ± 3.1 | 125.9 ± 6.2 |
| Absolute increase (% WT) | 32.7 | 31.0 | 10.3 | 19.7 | 6.5 | 32.7 | 25.5 | 21.3 |
| Relative increase | 1.93 | 1.61 | 3.67 | 2.75 | NC | 17.70 | 2.58 | 1.22 |

The results of the α-Gal A activity testing for the novel mutations N53K, Q57R. S62delinsLA, M96V. R112L, D155E, N228D, Q330P, V339A, K391E, and N408Y is shown in Table 3 below:

TABLE 3

Effect of Migalastat on α-Gal A Activity

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| N53K | 5143 ± 419 | 13895 ± 1270 | 0.0001 | 14.6 ± 1.0 | 38.6 ± 2.5 | 24.0 | 2.70 |
| Q57R | 20289 ± 995 | 26357 ± 916 | 0.0001 | 80.9 ± 3.8 | 105.0 ± 3.0 | 24.0 | 1.30 |
| S62delinsLA | 159 ± 27 | 8115 ± 810 | 0.0001 | 0.4 ± 0.1 | 21.3 ± 1.7 | 20.9 | 50.92 |
| M96V | 5458 ± 489 | 14612 ± 1009 | 0.0001 | 14.0 ± 1.2 | 38.1 ± 2.4 | 24.2 | 2.68 |
| R112L | BLD | 2364 ± 296 | 0.0001 | N/A | 7.5 ± 1.1 | 7.5 | NC |
| D155E | 1738 ± 78 | 6619 ± 337 | 0.0001 | 5.3 ± 0.3 | 19.8 ± 1.0 | 14.5 | 3.81 |
| N228D | 6264 ± 654 | 25816 ± 2273 | 0.0001 | 15.0 ± 1.5 | 63.2 ± 5.4 | 48.2 | 4.12 |
| Q330P | 5593 ± 320 | 12375 ± 664 | 0.0001 | 21.5 ± 1.6 | 45.8 ± 1.9 | 24.4 | 2.21 |
| V339A | 18918 ± 2287 | 25174 ± 2895 | 0.0339 | 48.8 ± 3.3 | 65.6 ± 4.2 | 16.8 | 1.33 |
| K391E | 7853 ± 735 | 15979 ± 1367 | 0.0001 | 20.4 ± 2.0 | 40.4 ± 2.9 | 20.0 | 2.03 |
| N408Y | 11158 ± 1707 | 23273 ± 2965 | 0.0001 | 40.9 ± 4.9 | 85.5 ± 7.7 | 44.6 | 2.09 |

The results of the α-Gal A activity testing for the novel mutations V22G, N34H, G80V. Q107R, Y152D, A156S. L189F. W204L. S238G, 1239M, A257V. P259Q. N320H, P323T. E338V. P380L, and T412P is shown in Table 4 below:

TABLE 4

Effect of Migalastat on α-Gal A Activity

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| V22G | 4663 ± 557 | 7150 ± 700 | 0.0067 | 15.5 ± 1.8 | 24.6 ± 2.8 | 9.0 | 1.53 |
| N34H | BLD | 1414 ± 100 | 0.0001 | N/A | 3.6 ± 0.2 | 3.6 | NC |
| G80V | 765 ± 56 | 2434 ± 333 | 0.0001 | 2.1 ± 0.1 | 6.4 ± 0.6 | 4.3 | 3.18 |
| Q107R | 24590 ± 1705 | 31193 ± 2248 | 0.0206 | 88.3 ± 7.0 | 109.8 ± 8.4 | 21.5 | 1.27 |
| Y152D | 2397 ± 346 | 6594 ± 294 | 0.0001 | 6.0 ± 0.9 | 16.7 ± 1.1 | 10.7 | 2.75 |
| A156S | 24479 ± 1666 | 31597 ± 2293 | 0.0111 | 66.7 ± 5.0 | 85.1 ± 53 | 18.4 | 1.29 |
| L189F | 22405 ± 1496 | 27388 ± 1605 | 0.0266 | 69.3 ± 3.9 | 84.6 ± 3.8 | 15.3 | 1.22 |
| W204L | 16126 ± 2360 | 32649 ± 3037 | 0.0002 | 36.9 ± 3.8 | 84.3 ± 5.9 | 47.4 | 2.02 |
| S238G | 5898 ± 877 | 25106 ± 1611 | 0.0001 | 18.7 ± 2.1 | 86.4 ± 7.2 | 67.7 | 4.26 |
| I239M | 4849 ± 622 | 24827 ± 3056 | 0.0001 | 13.9 ± 1.7 | 69.3 ± 6.9 | 55.5 | 5.12 |
| A257V | 16412 ± 1096 | 30313 ± 1981 | 0.0001 | 55.5 ± 3.3 | 99.9 ± 4.6 | 44.4 | 1.85 |
| P259Q | 13658 ± 1388 | 25935 ± 2020 | 0.0001 | 37.6 ± 3.4 | 73.6 ± 5.0 | 36.1 | 1.90 |
| N320H | 8554 ± 344 | 22149 ± 1050 | 0.0001 | 20.6 ± 1.3 | 52.9 ± 3.1 | 32.2 | 2.59 |
| P373T | 24566 ± 1350 | 29631 ± 1144 | 0.0008 | 59.0 ± 4.2 | 71.3 ± 4.1 | 12.3 | 1.21 |
| E338V | 11903 ± 541 | 21807 ± 845 | 0.0001 | 30.1 ± 1.7 | 54.8 ± 2.2 | 24.7 | 1.83 |
| P380L | 1424 ± 60 | 4248 ± 369 | 0.0001 | 3.4 ± 0.2 | 10.6 ± 1.0 | 7.1 | 2.98 |
| T412P | 639 ± 25 | 7159 ± 459 | 0.0001 | 1.7 ± 0.2 | 18.6 ± 1.2 | 16.9 | 11.21 |

In Tables 2-4, values for the meant standard error of the mean (SEM) were calculated. nmol/mg/hr indicates "nmoles of free 4-MU released per mg of protein per hour". WT indicates "wild-type". NC indicates "not calculable". N/A indicates "not applicable".

Baseline and 10 μM migalastat α-Gal A activity: Differences in the α-Gal A activity between lysates incubated in the absence and presence of 10 μM migalastat were determined using a one-tailed, Mann Whitney U test; an increase at 10 μM migalastat with a $p<0.05$ was considered significant. "BLD" indicates that the mean α-Gal A activity was below the limit of detection (<142 nmol/mg/hr).

Baseline α-Gal A activity (% WT)=(α-Gal A activity in mutant transfected cell lysates without migalastat÷α-Gal A activity in wild-type transfected cell lysates without migalastat)*100.

10 μM migalastat α-Gal A activity (% WT)=(α-Gal A activity in mutant transfected cell lysates incubated with 10 μM migalastat÷α-Gal A activity in wild-type transfected cell lysates without migalastat)*100.

Absolute increase (% WT)=is the 10 μM migalastat α-Gal A activity (% WT) minus the baseline α-Gal A activity (% WT).

Relative increase is the 10 μM migalastat α-Gal A activity in mutant transfected cell lysates÷baseline α-Gal A activity in mutant transfected cell lysates incubated without migalastat.

As can be seen from Table 2, the novel α-Gal A mutations D33H, G35A, Y88S, T194A, W204G, Y216S, Q250K, and R392T demonstrated an in vitro response to incubation with migalastat that met amenability criteria. Accordingly, patients with these mutations are expected to be treatable with migalastat therapy as described herein.

As can be seen from Table 3, the novel α-Gal A mutations D33H, G35A, Y88S, T194A, W204G, Y216S, Q250K, and R392T demonstrated an in vitro response to incubation with migalastat that met amenability criteria. Accordingly, patients with these mutations are expected to be treatable with migalastat therapy as described herein.

As can be seen from Table 4, the novel α-Gal A mutations V22G, N34H, G80V, Q107R, Y152D, A156S, L189F, W204L, S238G, 1239M, A257V, P259Q, N320H, P323T, E338V, P380L, and T412P demonstrated an in vitro response to incubation with migalastat that met amenability criteria. Accordingly, patients with these mutations are expected to be treatable with migalastat therapy as described herein.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treatment of Fabry disease in a human patient in need thereof, the method comprising administering to the patient a therapeutically effective dose of migalastat or a salt thereof, wherein the patient has an α-galactosidase A mutation selected from the group consisting of: D33H, G35A, Y88S, T194A, W204G, Y216S, Q250K, and R392T.

2. The method of claim 1, wherein the migalastat or salt thereof is administered to the patient every other day.

3. The method of claim 1, wherein the patient is administered 100 to 150 mg free base equivalent of the migalastat or salt thereof every other day.

4. The method of claim 1, wherein the patient is administered 150 mg of migalastat hydrochloride every other day.

5. The method of claim 1, wherein the patient is male.

6. The method of claim 1, wherein the patient is female.

7. The method of claim 1, wherein the mutation is disclosed in a pharmacological reference table.

8. The method of claim 7, wherein the pharmacological reference table is provided in a product label for a migalastat product approved for the treatment of Fabry disease.

9. The method of claim 1, wherein the mutation is D33H.

* * * * *